United States Patent
Pile-Spellman et al.

(10) Patent No.: US 11,471,596 B2
(45) Date of Patent: Oct. 18, 2022

(54) SYSTEMS METHOD AND METHODS FOR PERFUSING TISSUE DISTAL TO AN ARTERIAL OCCLUSION

(71) Applicants: John Pile-Spellman, Pelham, NY (US); Jae H. Choi, Mineola, NY (US)

(72) Inventors: John Pile-Spellman, Pelham, NY (US); Jae H. Choi, Mineola, NY (US)

(*) Notice: Subject to any disclaimer, the term of this patent is extended or adjusted under 35 U.S.C. 154(b) by 488 days.

(21) Appl. No.: 16/369,217

(22) Filed: Mar. 29, 2019

(65) Prior Publication Data
US 2019/0298919 A1  Oct. 3, 2019

Related U.S. Application Data

(60) Provisional application No. 62/649,719, filed on Mar. 29, 2018.

(51) Int. Cl.
*A61M 5/172* (2006.01)
*A61M 5/168* (2006.01)

(52) U.S. Cl.
CPC ....... *A61M 5/1723* (2013.01); *A61M 5/16836* (2013.01); *A61M 2005/1726* (2013.01); *A61M 2205/332* (2013.01); *A61M 2205/3334* (2013.01); *A61M 2205/3344* (2013.01); *A61M 2205/3368* (2013.01); *A61M 2205/3379* (2013.01); *A61M 2205/502* (2013.01); *A61M 2205/52* (2013.01)

(58) Field of Classification Search
CPC .............. A61M 5/1723; A61M 60/31; A61M 5/16836; A61M 1/1603; A61M 1/3607; A61M 1/1613; A61M 2005/1726
See application file for complete search history.

(56) References Cited

U.S. PATENT DOCUMENTS

| 2006/0167398 A1 | 7/2006 | Solar |
| 2011/0209764 A1* | 9/2011 | Uber .................... A61N 5/1007 137/1 |

(Continued)

FOREIGN PATENT DOCUMENTS

| WO | WO2016/149653 | 9/2016 |
| WO | WO/2017/009668 | 1/2017 |

(Continued)

OTHER PUBLICATIONS

MYOtherm XP, Medtronic, Dec. 2017.
(Continued)

*Primary Examiner* — Bhisma Mehta
*Assistant Examiner* — John J Crawford
(74) *Attorney, Agent, or Firm* — Antonio Papageorgiou; Lombard & Geliebter LLP

(57) ABSTRACT

This application describes a method and device for safely, effectively, perfusing distal to occluded arteries, based on diagnostic information from the catheter-perfusion-system based on sensors, effectors, controllers and algorithms included, with particular attention to the specific characteristics of the tissue and the fluid. Key actionable physiological values for the tissue can be calculated and derived. They include the auto-regulatory curve, with Upper and Lower limits of Auto regulation, vascular reserve, and collateral flow reserve and as auto-regulation exhaustion.

18 Claims, 16 Drawing Sheets

(56) References Cited

U.S. PATENT DOCUMENTS

| | | | | |
|---|---|---|---|---|
| 2012/0253211 A1* | 10/2012 | Brady | ............... | A61M 60/31 |
| | | | | 604/6.11 |
| 2013/0165736 A1 | 6/2013 | Mohl | | |
| 2013/0331916 A1* | 12/2013 | Pile-Spellman | ........ | A61M 5/44 |
| | | | | 607/106 |
| 2016/0206816 A1* | 7/2016 | Pile-Spellman | ........ | G16Z 99/00 |
| 2017/0189654 A1 | 7/2017 | Schwartz et al. | | |
| 2017/0333685 A1 | 11/2017 | Kassab | | |

FOREIGN PATENT DOCUMENTS

| | | |
|---|---|---|
| WO | WO2017/048733 | 3/2017 |
| WO | WO-2017055450 A1 * | 4/2017 |

OTHER PUBLICATIONS

PCT International Search Report PCT/2019/024773.
PCT International Preliminary Report on Patentability PCT/2019/024773.
European Search Report for International Application No. 19778398.8 (PCT/US2019/024773), dated Nov. 5, 2021, 10 pages.

* cited by examiner

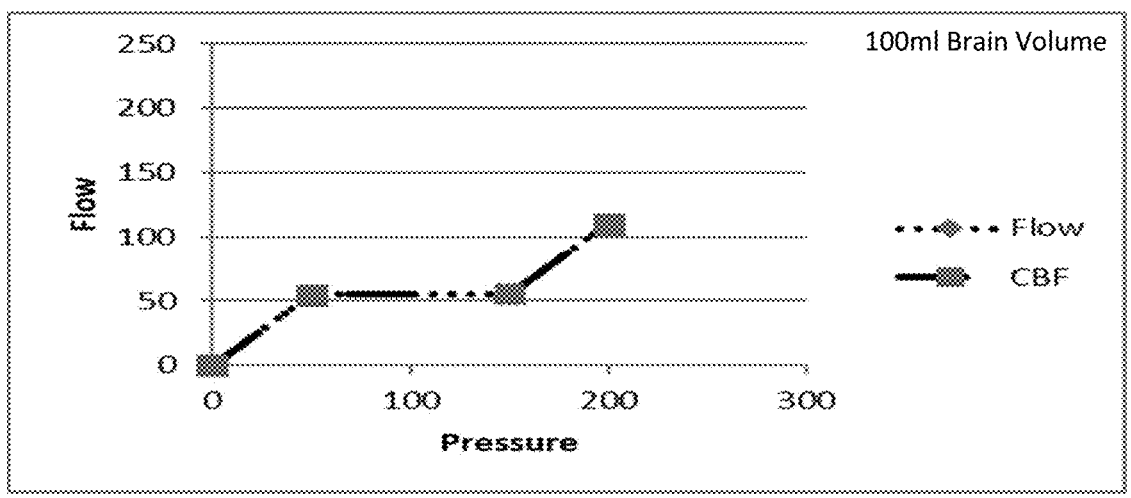
Fig. 5A1
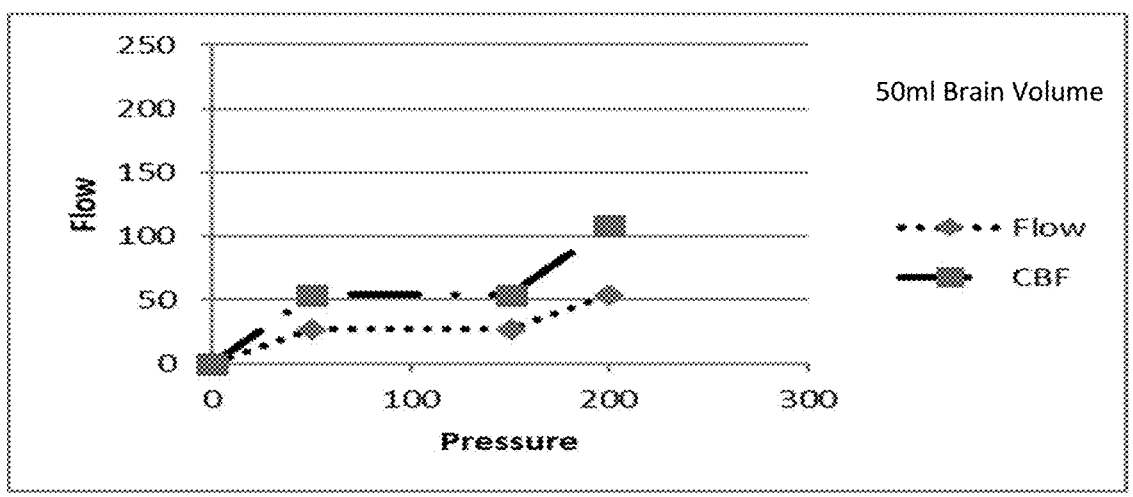
Fig. 5A2
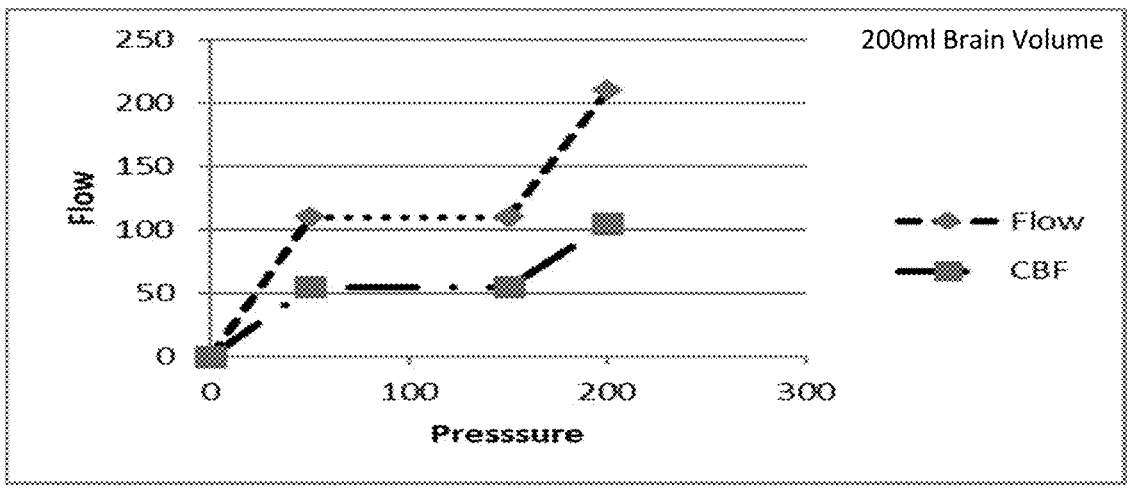
Fig. 5A3

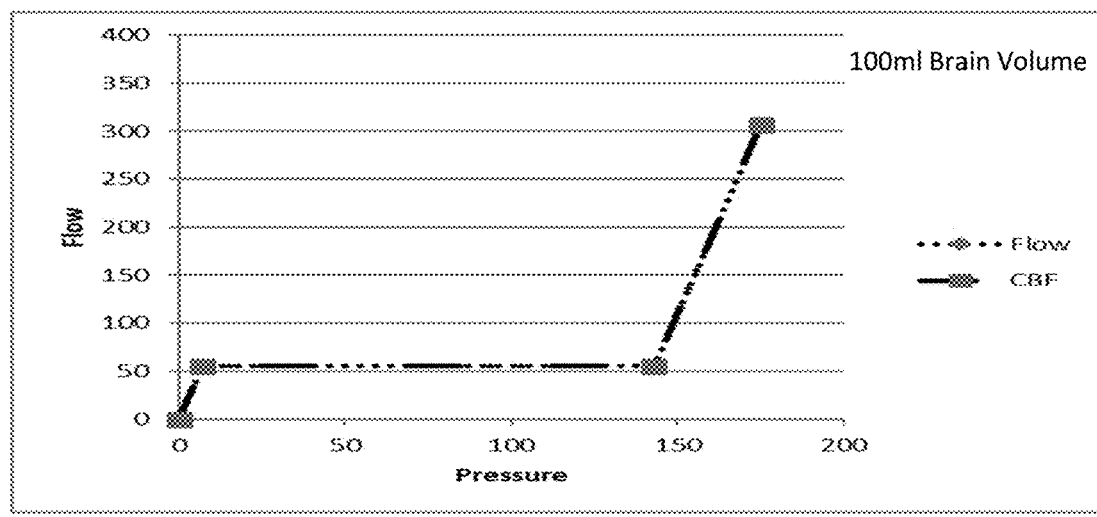
Fig. 5B1
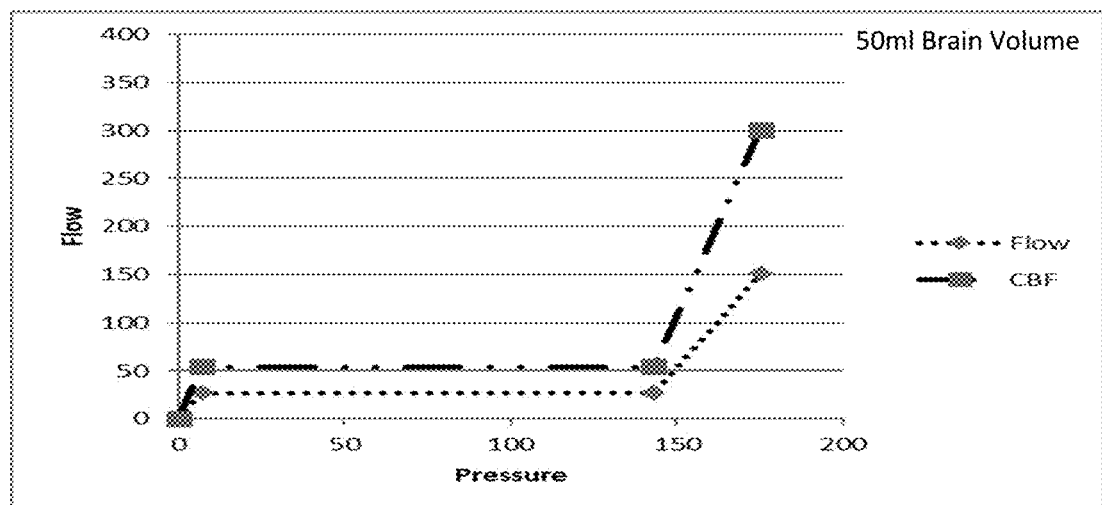
Fig. 5B2
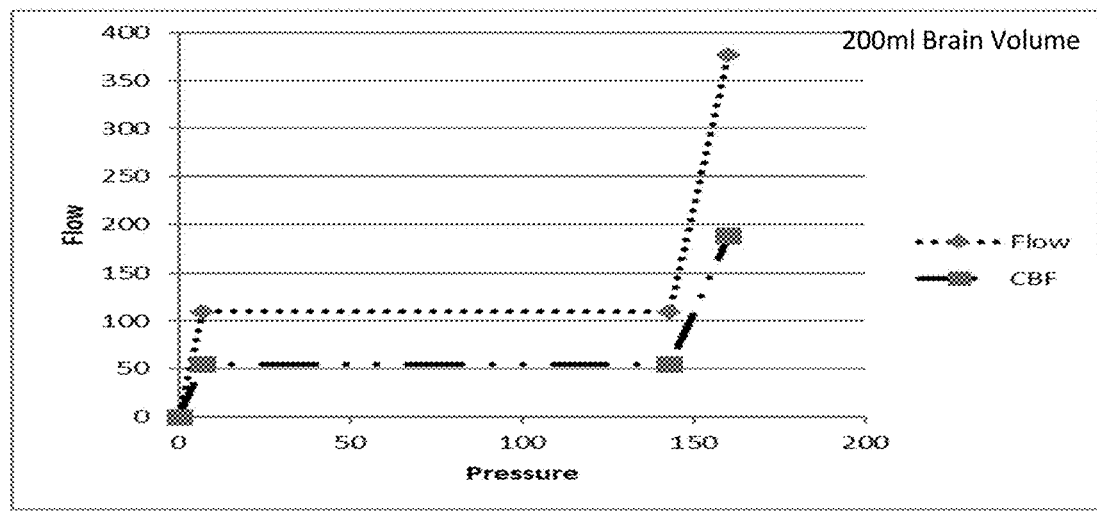
Fig. 5B3

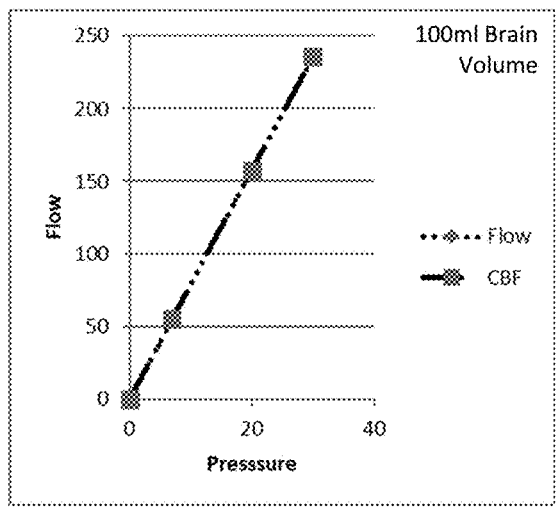
Fig. 5C1
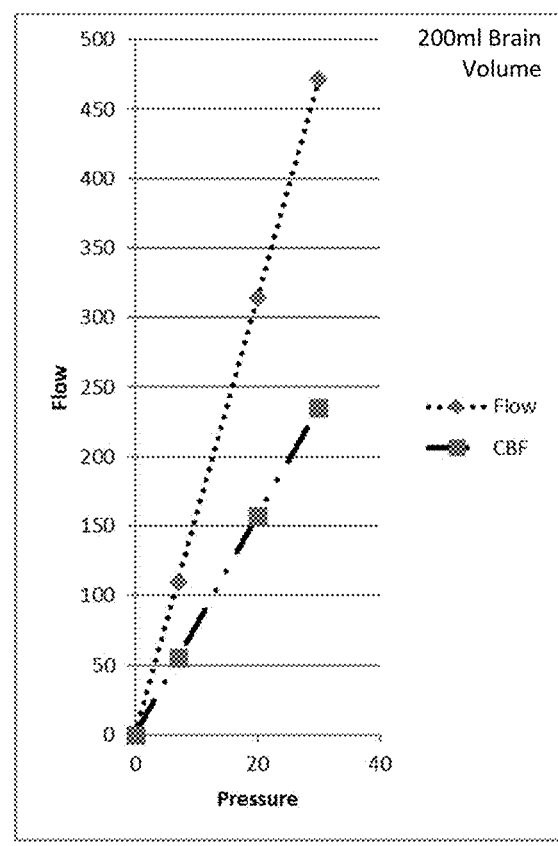
Fig. 5C3
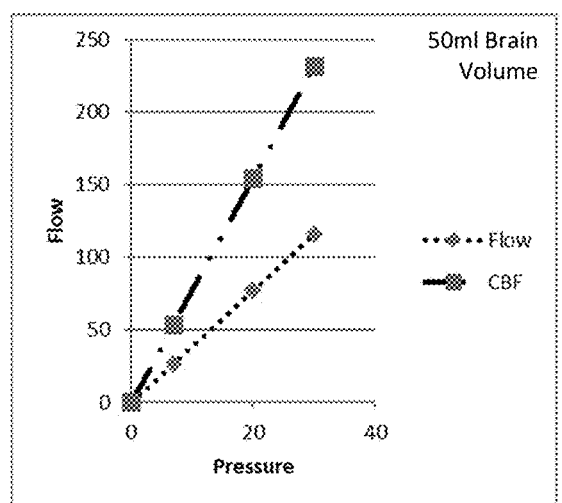
Fig. 5C2

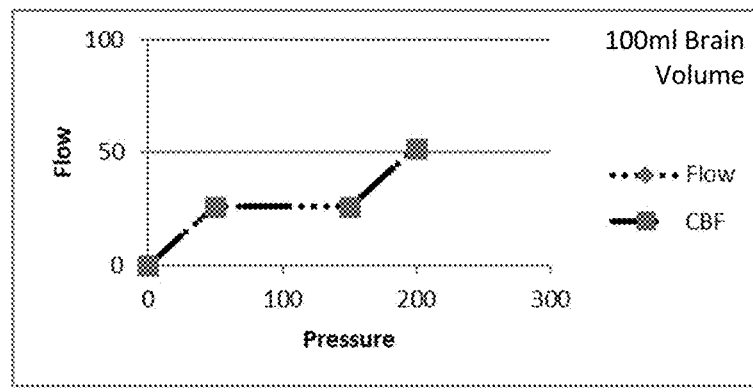
Fig. 5D1
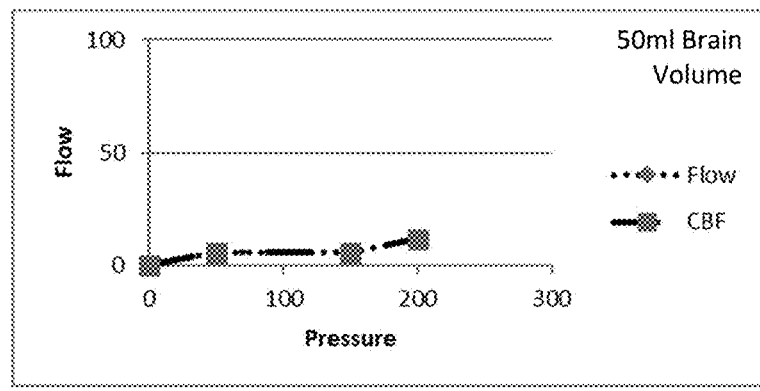
Fig. 5D2
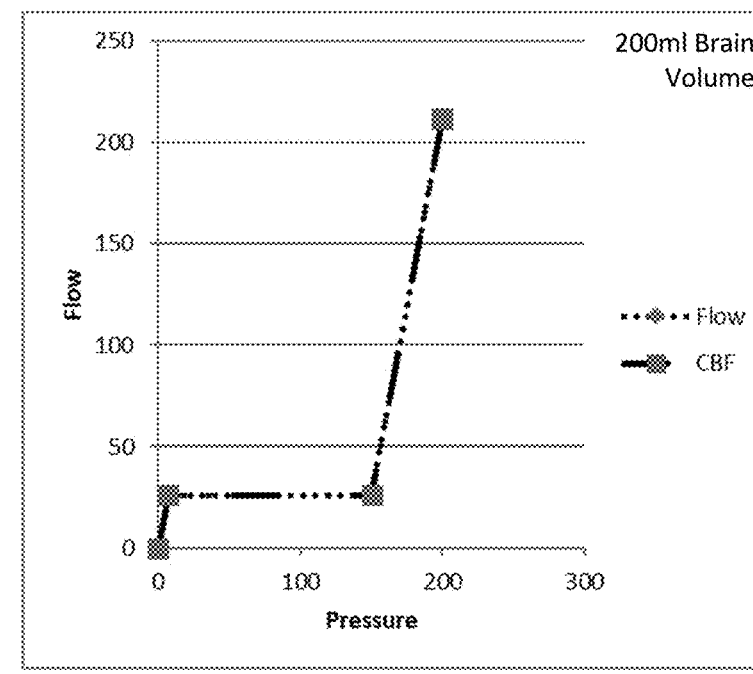
Fig. 5D3

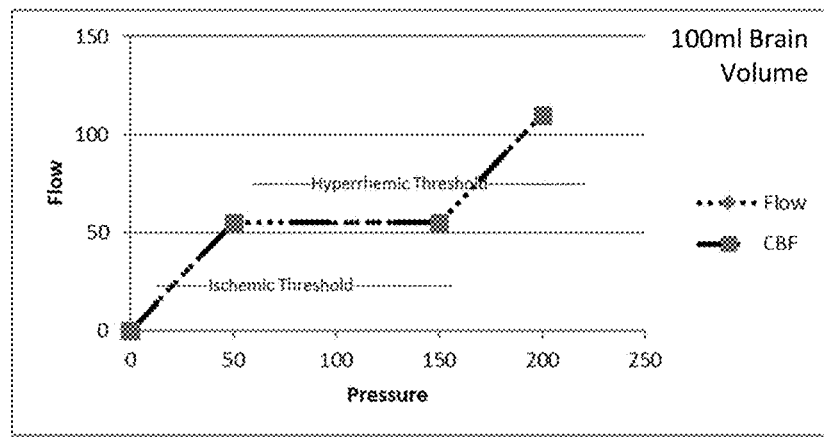
Fig. 5E1
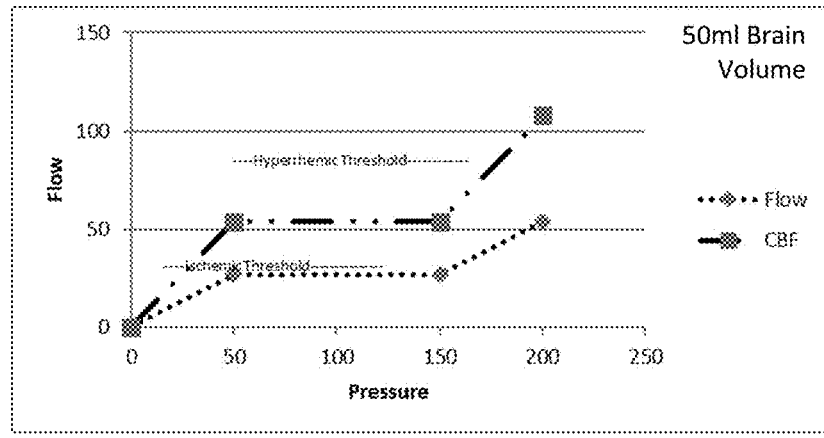
Fig. 5E2
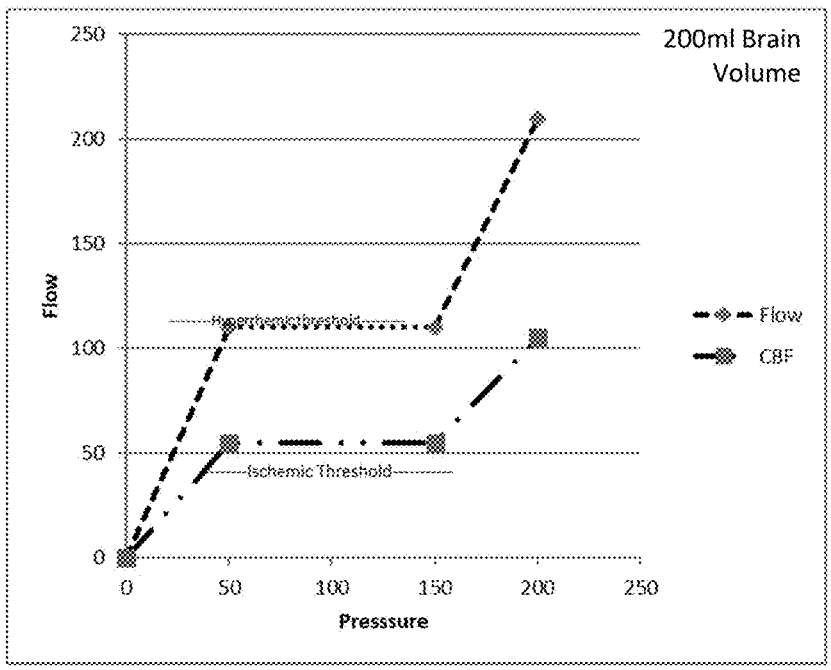
Fig. 5E3

SYSTEMS METHOD AND METHODS FOR PERFUSING TISSUE DISTAL TO AN ARTERIAL OCCLUSION

BACKGROUND

The present application relates to systems and corresponding methods for perfusing tissue distal to occluded arteries, and more particularly catheter-based systems that provide diagnostic information based on sensors, effectors, controllers and processes included with such system, with particular attention to the specific characteristics of the tissue being perfused and the perfusion fluid.

The present application relates to systems and corresponding methods for perfusing tissue distal to occluded arteries, and more particularly catheter-based systems that provide diagnostic information based on sensors, effectors, controllers and processes included with such system, with particular attention to the specific characteristics of the tissue being perfused and the perfusion fluid.

Methods for assessing tissue condition after vascular occlusions exist. For instance, angiographic assessment, provocative testing with temporary test occlusion and systemic hypotension, stump pressures, and radio-nuclide imaging have been used to assess adequacy of collateral flow prior to therapeutic closure. Perfusing partially occluded vessels and the measuring physiological parameters has also been done. Pressure gradients, flow gradients, (Fractional Flow Reserve, FFR) have also been used to determine the need for elective revascularization of narrowed, non-occluded vessels. FFR generally refers to a whole cardiac cycle pressure-derived index of the maximum achievable blood flow in a coronary artery with a stenosis expressed as a ratio of maximum achievable blood flow if that artery were normal.

All of the above assessments, however, are indices based on static measurements with linear expectations of the pressure, flow, resistance interactions, without adjustments for viscosity, $[O_2]$, volume of the tissue, or state of auto-regulation. Additionally, pharmacologic manipulations often used to obtain these measurements lay outside the range of physiological responses, (adenosine, dihydropyridine etc). These premises are not true for tissues with auto-regulation such as brain, kidneys, and heart-exactly the tissues where the information is most critical. Additionally, within each of these tissues, changes such as age, chronic hypertension, or tissue pressure, oxidative stress have a profound effect. The above methods, however, only provide rough estimates and are only useful for projecting the outcome under the best clinical conditions.

Accordingly, there is a need for systems for perfusing tissue distal to an occlusion, that obtain or otherwise derive information in real-time for, for example, tissue rescue, including normal, damaged and dead tissue in the vascular territory, without adding additional trauma. Such actionable physiological information beneficially makes infusion and/or reperfusion safer and more effective, and/or provide for inducing ischemic tolerance, for tissue to better withstand ischemic injury and secondary injury related to ischemia and reperfusion.

SUMMARY

This application discloses systems and corresponding methods allowing safe and effective perfusion distal to an arterial occlusion. These systems address many presently identified limits of this procedure. Perfusion may accomplished with a variety of systems, including the systems disclosed in U.S. Pat. No. 8,343,097, entitled "System and Method for Intravascular Cooling", as well as U.S. Patent Publication No. 20160206816, entitled "Devices for Estimating Regional Metabolic Rate of Organs Based on Heat Generation and for Estimating Regional Blood Flow(s) for the Volume(s) of Tissue Perfused", which are hereby incorporated herein by reference. The inventive system according to at least one embodiment includes a fluid conduit, such as a catheter, with sensors attached thereto or associated therewith, a controller, a pump and a fluid source, communicatively interconnected and programmed to perform the method(s) and/or execute algorithms for controlling the pump based on the collected data from the sensors and input from the operator or lookup table. The device does this by determining the perfusate and tissue perfusion parameters of the perfused tissue, and perfusing within these parameters. These parameters may include: A. Perfusate parameters; 1) viscosity, 2) temperature, 3) $[O_2]$, 4) $[CO_2]$, and, 5) other vaso-active materials, as well as B. Tissue parameters: 1) volume perfused/pressure/volume of tissue curve, and 2) estimated shape of auto-regulation, or dys-auto-regulation curves.

Clinically actionable information and therapeutic manipulations may be obtained or otherwise derived by these systems and method. Such information may include: 1) functional status of tissue auto-regulation, 2) amount of tissue at being perfused, 3) blood pressure parameters needed to avoid transgressing ischemic or baro-trauma thresholds, 4) $O_2$ and flow requirements needed. Additionally, vascular compliance and collateral circulations status can be estimated.

BRIEF DESCRIPTION OF THE DRAWINGS

FIGS. 5A1-5E3 are charts showing idealized curves Perfusion Pressure, (P, mmHg) vs. Flow, (Q, cc/min), for Brain curves under various situations and conditions.

DETAILED DESCRIPTION

Figure 1:
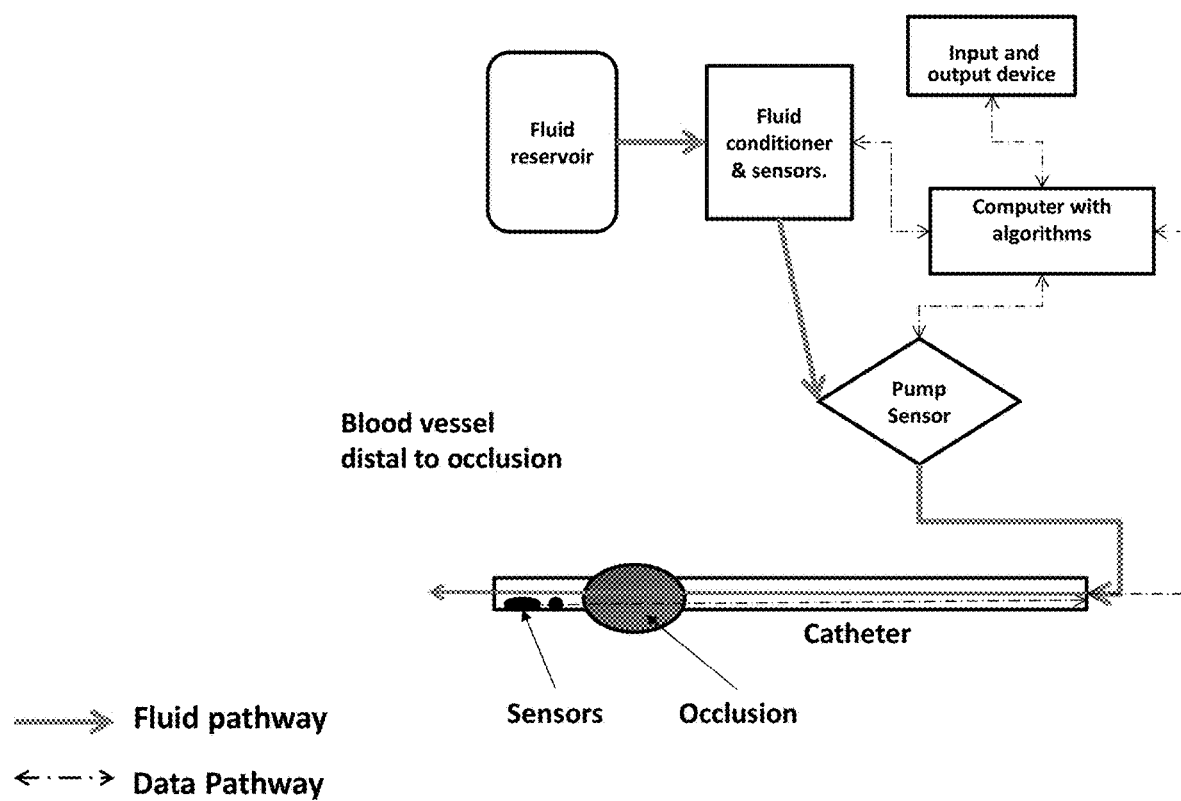
FIG. 1 is a diagram of a system for perfusing tissue distal to an occlusion according to at least one embodiment of the systems disclosed herein.

When perfusing tissue distal to occluded blood vessel or where the blood vessels are purposefully occluded, actionable information is limited. In patients with occlusion, perfusion distal to an occlusion would offer a wide array of potential powerful therapeutic interventions such as local hypothermia, cell free reperfusion, and super selective drug and dissolved gas treatment. Perfusing distal occlusions has been limited due to the uncertainty regarding the safety and effectiveness of such maneuvers. Operationally, selective perfusion distal to an occlusion would require key real-time information such as the proper pressure, flow rate, amount of tissue perfused, viscosity of fluid, $[O_2]$, tissue temperature, and auto-regulatory state of the tissue. Such information is desirable to avoid problems such as catastrophic rupture of the blood vessel, malignant edema, under and or over perfusion.

Normal tissue has the self-reliant auto regulation, protecting it from barotraumas, and ensuring adequate blood flow. Dead tissue on the other hand is likely hyper-sensitive to baro or flow related-trauma developing bleeds and cytotoxic edema, whereas ischemic-damaged tissue is extremely pressure dependent on both ends of the curve—not getting enough blood or damaging hyperemia. Additionally, post ischemic hyperemia, and ischemic reperfusion injury may be at play. Blood-perfusate characteristics such as viscosity and $pO_2$, $CO_2$, as well as effective tissue volume, tissue metabolic state and temperature all have a profound effect on the of volume and pressures required for effective and safe perfusion. To date, little information is available to guide professionals in this regard. Accordingly, the systems disclosed herein generally provide such information, preferably in real time, for perfusing tissue distal to a blood vessel occlusion.

Additionally, tissue can be conditioned to better withstand ischemia. Conditioning can be a powerful tissue protective method with endogenous properties, similar to tissue protection via hypothermia. Conditioning may be performed before (pre-conditioning), during (intra- or per-conditioning), and after the ischemic event (post-conditioning). Only intra/per-conditioning and post-conditioning are clinically practical methods, whereas intra/per-conditioning is more effective than post-conditioning. Conditioning may be performed by repeated exposure of tissue to ischemia with regular perfusion in between the noxious stimuli. Thus far no devices or systems exist to effectively and practically apply conditioning to tissue at acute risk for ischemia/reperfusion and related injuries. Accordingly, the inventive systems disclosed herein may further be operable to provide tissue conditioning, preferably automatically or semi-automatically based on the real time information obtained or derived by the system.

Similar issues of perfusing tissues that effectively taking over the perfusion of organs are confronted with organ transplant transportation, and cardio-pulmonary bypass circuits, and have been addressed with guidelines from animal and clinical trials. Accordingly, although the embodiments of the present application may be discussed in relation to the brain and brain injuries, it is understood that the systems may be used in relation to other organs and are therefore not limited in this regard.

Referring to FIG. 1, a diagram of a system for perfusing tissue distal to an occlusion according to at least one embodiment is shown. The catheter 101 is placed in a blood vessel and the tip of the catheter 101 is navigated distal to an occlusion 102. The catheter 100 has a data pathway and a fluid pathway. The sensors 104 of this data pathway can be in the distal end of the catheter, or proximally in the pump/pump sensor(s) 106/108. The sensors 104/108 may include, pressure, flow rate, and can include $[O_2]$, temperature and sensors for capturing other characteristics of the tissue and/or perfusate in situ, preferably in real time. The system may further include a controller 100 programmed with software operable to execute an algorithm that make she system operable to collect the data desired for perfusion, as discussed herein, and to operate the actuators that control the pump 106, to perform the desired functions, as also discussed herein, preferably in real time. The controller may compute certain input parameters from look-up tables or from input from operators of the system. The system further includes an input device 112, such as a switch(es), rotary dial(s), keypad or keyboard, touch screen, etc., and output devices 114 for the display of information, such as an LCD monitor, a printer, etc.

The system may further store one or more predefined sets of instruction with regard to temperature, flow rate, time, etc. in a computer memory device, which may be implemented by the system upon selection by the user. As discussed herein, the sets of instruction may include sequence and timing for the operating parameters of the system, for example, for incrementally cooling and heating the infusate and/or the site of interest, maintaining temperature of the infusate and/or the site of interest, controlling pressure and flow rates, as well as any of the other variables or parameters discussed herein. The memory may further store the data collected and/or estimated by the system, for example, in a database. As can also be seen, the system includes an infusate reservoir 116 for storing the infusate and preferably fluid condition(s) 118 with associated sensor (s) 120.

Figure 2:
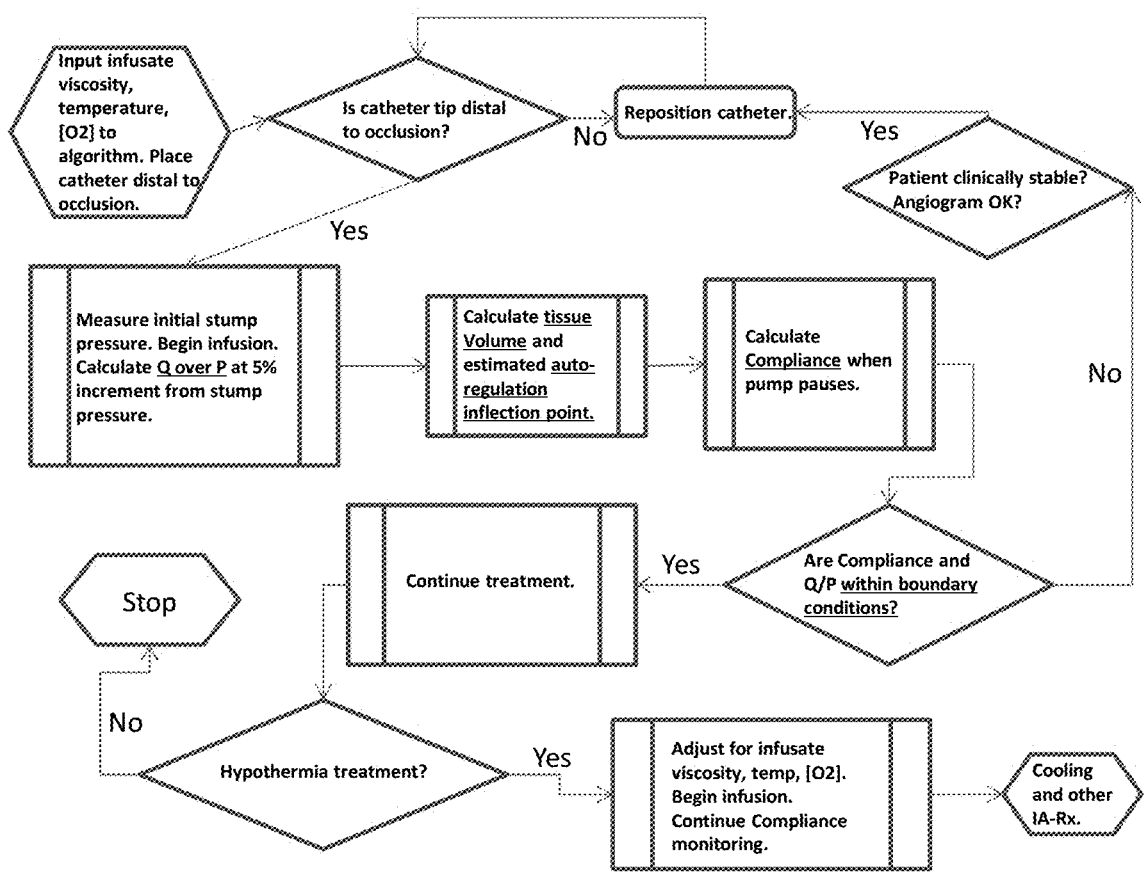
FIG. 2 is a flowchart of a method performed by a system operation for perfusing tissue distal to an occlusion according to at least one embodiment of the methods disclosed herein.

FIG. 2 is a flowchart depicting the operation of the system operation with regard to determining the parameters of the infusion fluid for perfusion. The expected effects on flow characteristics may be calculated, and threshold/alarms limits determined by the system. Generally, once the catheter is placed distal to occlusion, stump pressure may then be determined, and the infusion may begin and incrementally increased based on feedback from the system sensors. The infusate volume/pressure/min curve may then be determined, which, with embedded processes, used to calculate the physiologically meaningful infusate volume/pressure/min/volume of tissue curves, as discussed herein. The controller may then control the pump to supply safe perfusion during whatever manipulations are being considered.

The process generally begins with input from the user or based no information obtained by the system via the sensor (s), such as infusate viscosity (which may be determined in situ or using lookup tables, temperature of the infusate, and $[O_2]$ of the infusate. Thereafter, the catheter may be introduced distal to the occlusion and the system may then measure parameters, such as stump pressure. Infusion may then begin with flow and pressure calculated and applied at 5% increments from the stump pressure. Based on sensor feedback, tissue volume may then be calculated and an autoregulation inflection point may be estimated. Compliance and Q/P may be tested periodically and adjusted as needed throughout the treatment.

Figure 3:
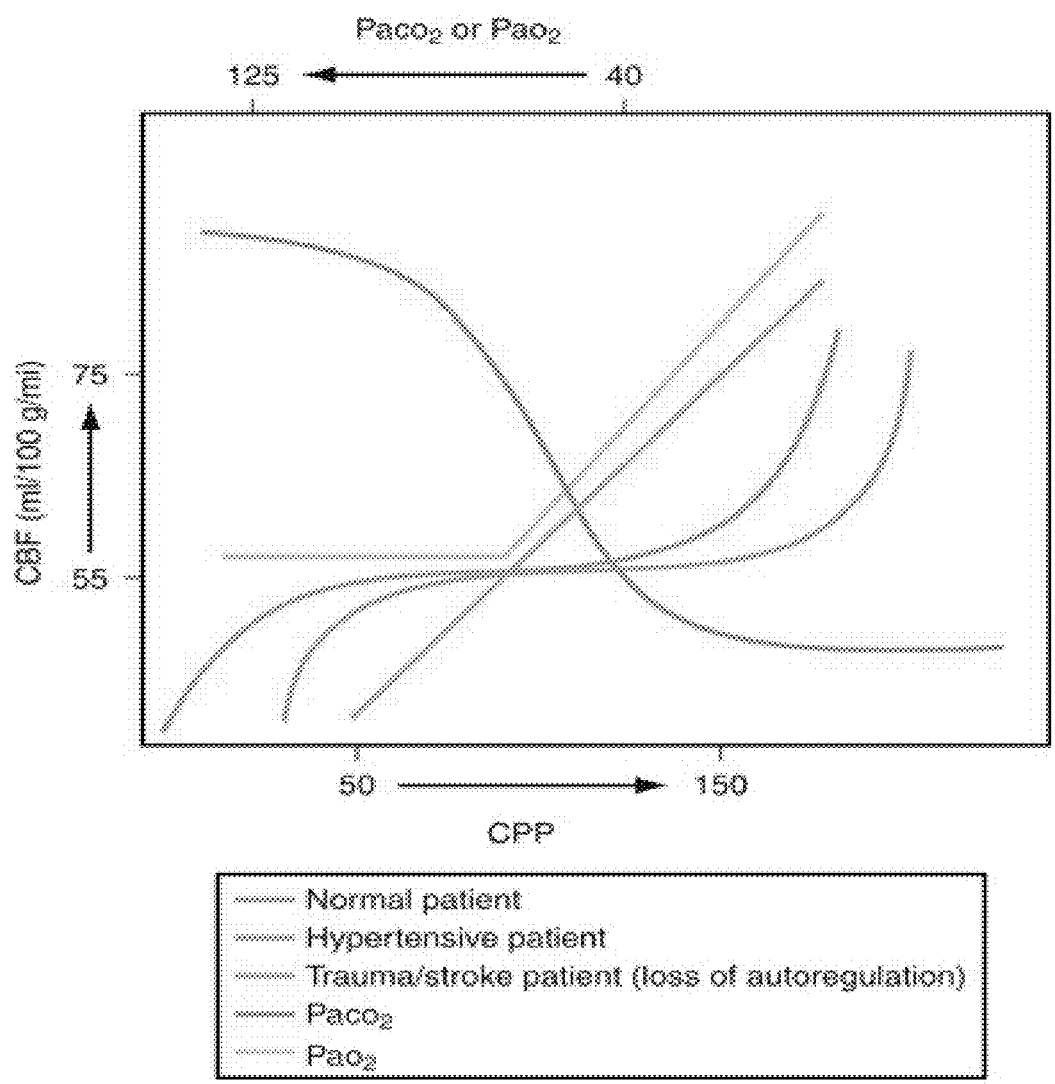
FIG. 3 is a chart summarizing Auto-Regulation of CBF (Pressure/Perfusion for 100 cc brain volume) curves for brain tissue) under different conditions.

FIG. 3 is a chart summarizing Auto-Regulation of CBF (Pressure/Perfusion for 100 cc brain volume) curves for brain tissue) under different conditions. The curves are for whole blood infusate, with alterations in [$O_2$], [$CO_2$], functioning and non-functioning auto-regulation, but do not explore effects of viscosity, or temperature and is normalized for 100 cc of brain tissue perfused.

Figure 4:
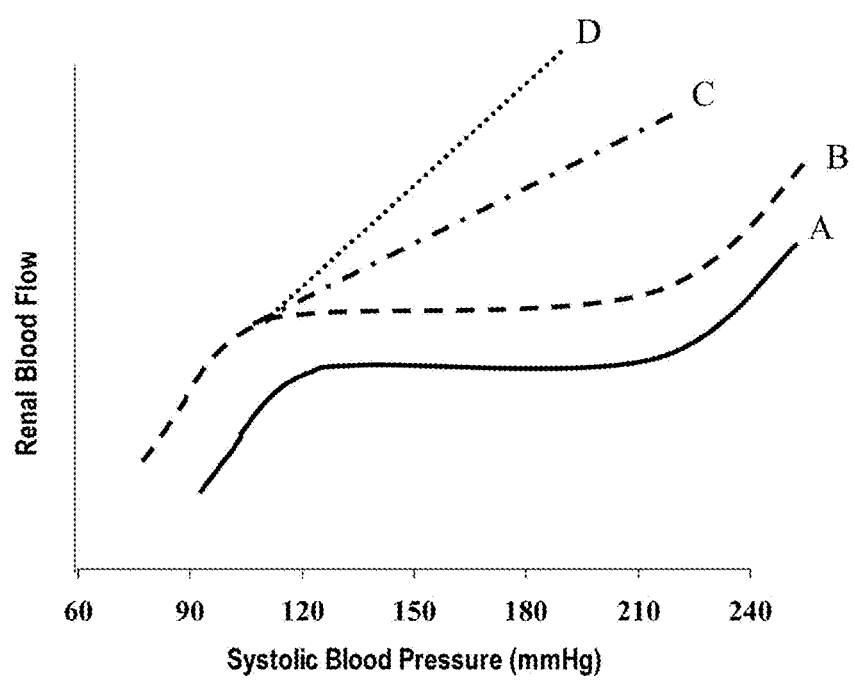
FIG. 4 is a chart that depicts renal experimental data, Auto Pressure Perfusion curves for kidneys under different experimental conditions.

FIG. 4 depicts data from renal experiments and, more particularly, Auto Pressure Perfusion curves for kidneys under different experimental conditions. Note that the shape, slope and intercepts change related to the tissue and infusate conditions. More specifically, the chart shows the spectrum of pressure flow relationships in the renal vascular bed in hypertension. Pattern A represents the normal renal autoregulatory responses observed in uncomplicated hypertension and shows the constancy of renal blood flow (RBF) despite BP changes within the autoregulatory range. Pattern B indicates the ambient renal vasodilation but preserved autoregulation after uninephrectomy. Pattern C illustrates the impaired RBF autoregulatory responses observed in the 5/6 renal ablation model. Pattern D shows the complete loss of renal autoregulation in 5/6 renal-ablated rats treated with dihydropyridine CCBs. Although RBF is depicted as the dependent variable, the same relationships are expected to obtain for PGC, given that the autoregulatory resistance changes are confined to the preglomerular vasculature.

FIGS. 5A1-5E3 show idealized curves for Perfusion Pressure, (P, mmHg) vs. Flow, (Q, cc/min), for Brain curves under various situations and conditions. The conditions explored include a) alterations in brain volume, b) brain temperature, c) brain with intact and absent auto regulation, as well as the perfusate being adequately d) oxygenated blood, or saline and e) deoxygenated saline. It is appreciated immediately that tissue perfusion is a complex. Vascular resistance to insure adequate immediate tissue [$O_2$] and protect it from baro/hyperemic trauma.

FIGS. 5A1-5A3 show, with regard to tissue with intact auto regulation AND perfused with normally oxygenated blood at a normal hematocrit and normal temperature, the effect of different tissue mass on flow at given pressures.

The FIG. 5A1 plot is normalized to 100 cc of brain.
The FIG. 5A2 curve is normalized to 50 cc of brain.
The FIG. 5A3 curve is normalized to 200 cc of brain.

FIGS. 5B1-5B3 are idealized curves showing, with regard to tissue with intact auto regulation AND perfused with adequately oxygenated saline, the effect of different volume on flow at given pressures. Adequately oxygenated saline generally refers to that which carries enough $O_2$ for tissue metabolism, or approximately 4 cc/100 cc. Note that low viscosity saline takes significantly less pressure to perfuse the same amount of fluid.

The FIG. 5B1 plot is normalized to 100 cc of brain.
The FIG. 5B2 curve is normalized to 50 cc of brain
The FIG. 5B3 curve is normalized to 200 cc of brain FIGS. 5C1-5C3 are idealized curves showing, with regard to tissue with intact auto regulation AND perfused with deoxygenated saline, the effect of different volume on flow at given pressures. Note that the low viscosity saline takes significantly less pressure to perfuse the same amount of fluid, and it, with deoxygenated fluid, the tissue acts similar to situations with no auto regulation.

The FIG. 5C1 plot is normalized to 100 cc of brain.
The FIG. 5C2 curve is normalized to 50 cc of brain.
The FIG. 5C3 curve is normalized to 200 cc of brain.

FIGS. 5D1-5D3 are idealized curves showing tissue with intact auto regulation AND the effect of brain/perfusate temperature with intact auto regulation each with 100 cc brain volume. Note as the temperature falls the Cerebral Metabolic Rate (CMR) falls which in turn causes a drop in blood flow.

FIG. 5D1 brain/perfusate temperature 33° C. perfused with adequately oxygenated blood.
FIG. 5D2 brain/perfusate temperature 26° C. perfused with adequately oxygenated blood.
FIG. 5D3 brain/perfusate temperature 33° C. perfused with adequately oxygenated saline.

FIGS. 5E1-5E3 are similar to 5A1-5A3 with the addition of idealized ischemic, and hyperemic thresholds. The plots show, with regard to tissue with intact auto regulation AND perfused with normally oxygenated blood at a normal hematocrit and normal temperature, the effect of different tissue mass on flow at given pressures. The ischemic thresholds are idealized as equal to 20 cc adequately oxygenated blood/100 cc of brain/min. Hyperemic Thresholds are of two types: Hypertensive, from Pressures >1.5× normal, and High flow angiopathy from flows with high Reynolds number.

As shown in FIG. 5B1-5B3 it possible to deliver sufficient oxygen to tissue with intact auto regulation AND perfused with adequately oxygenated saline. The ischemic thresholds are idealized as equal to 20 cc adequately oxygenated blood/100 cc of brain/min. The plots will be similar to the plots depicted in FIG. 5E1-5E3. The amount of oxygen actually extracted, is only 4 cc, and can also be delivered as dissolved oxygen using hyperbaric methods. Hyperemic Thresholds appear to be of two types: Hypertensive, from Pressures >1.5× normal, and High flow angiopathy from flows with high Reynolds number, FIGS. 6-18 show Bulk Flow vs. pressure, and flow per unit volume of tissue vs. curves scenarios used. Note, the units in these Bulk Flow graphs are cc of flow/min, which is not the same as used in critical physiological measures, Cerebral Blood Flow, etc., which are cc of flow/min/100 cc of tissue.

Figure 6:
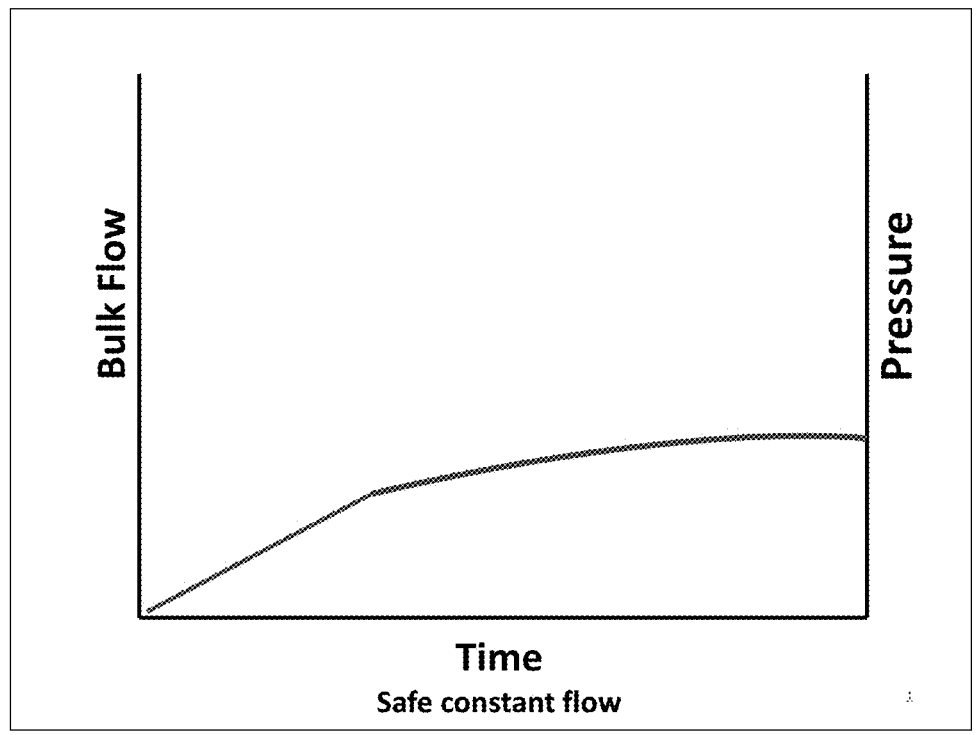
FIG. 6 is a chart depicting Safe Flow and Pressure over time at constant flow rate.

FIG. 6 shows Safe Flow and Pressure over time at constant flow rate.

Figure 7:
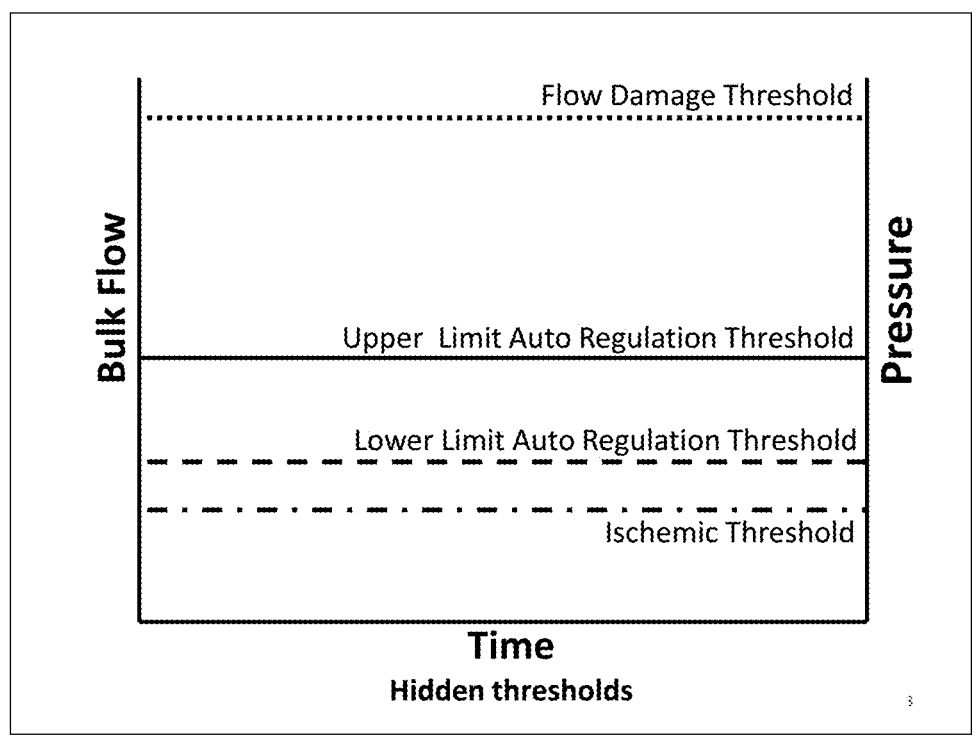
FIG. 7 is a chart depicting Bulk Flow Pressure/Time; showing the Hidden Thresholds.

FIG. 7 shows Bulk Flow Pressure/Time; showing the Hidden Thresholds. The specific values of thresholds are dependent of the amount of tissue being perfused, [$O_2$], etc.

Figure 8:
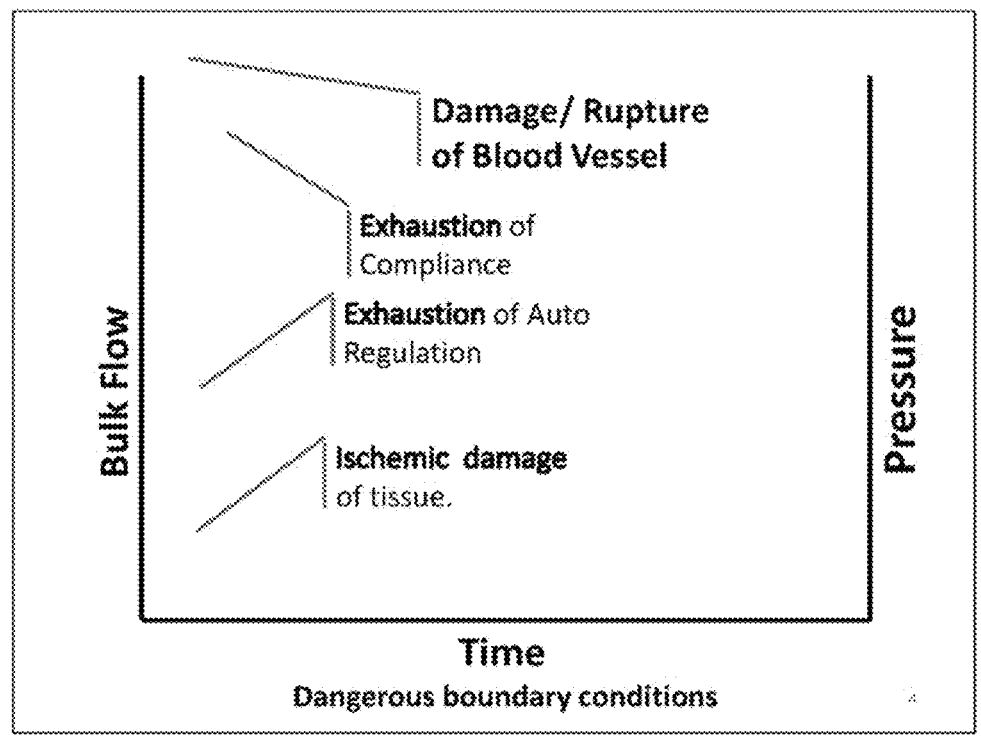
FIG. 8 is a chart depicting Bulk Flow: Pressure/Time; some expected outcome if Dangerous Boundary Conditions are transgressed.

FIG. 8 Bulk Flow: Pressure/Time; some expected outcome if Dangerous Boundary Conditions are transgressed.

Figure 9:
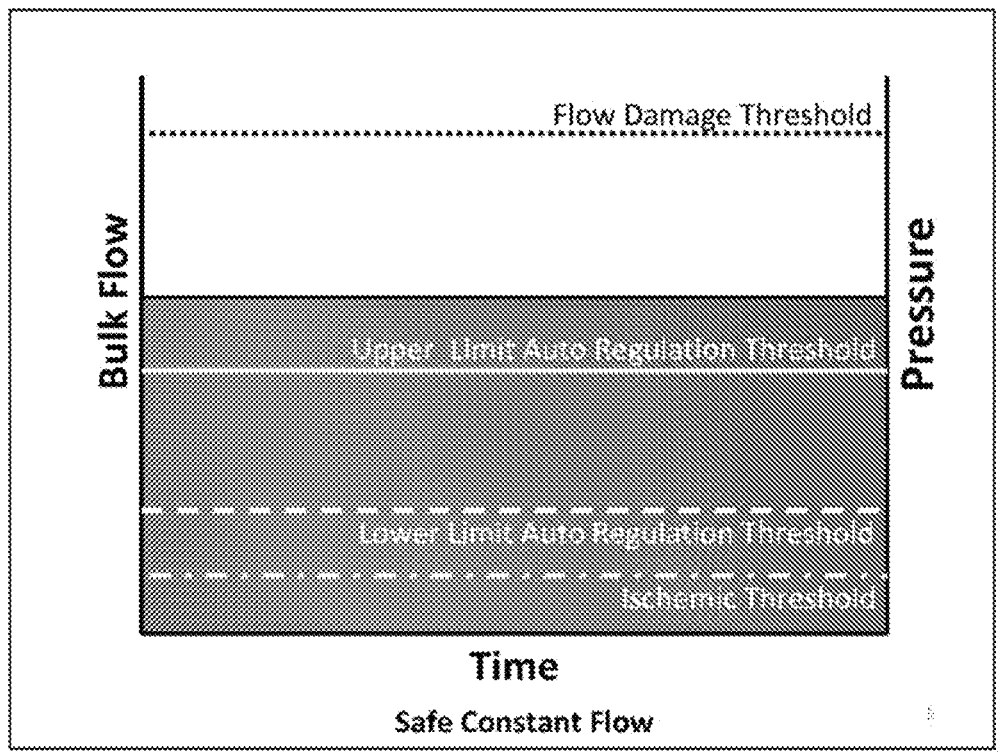
FIG. 9 is a chart depicting Bulk Flow: Pressure/Time; Safe Constant Flow; similar to FIG. 6 with the physiological thresholds in place using the device disclosed.

FIG. 9 shows Bulk Flow: Pressure/Time; Safe Constant Flow; similar to FIG. 6 with the physiological thresholds in place using the device disclosed.

Figure 10:
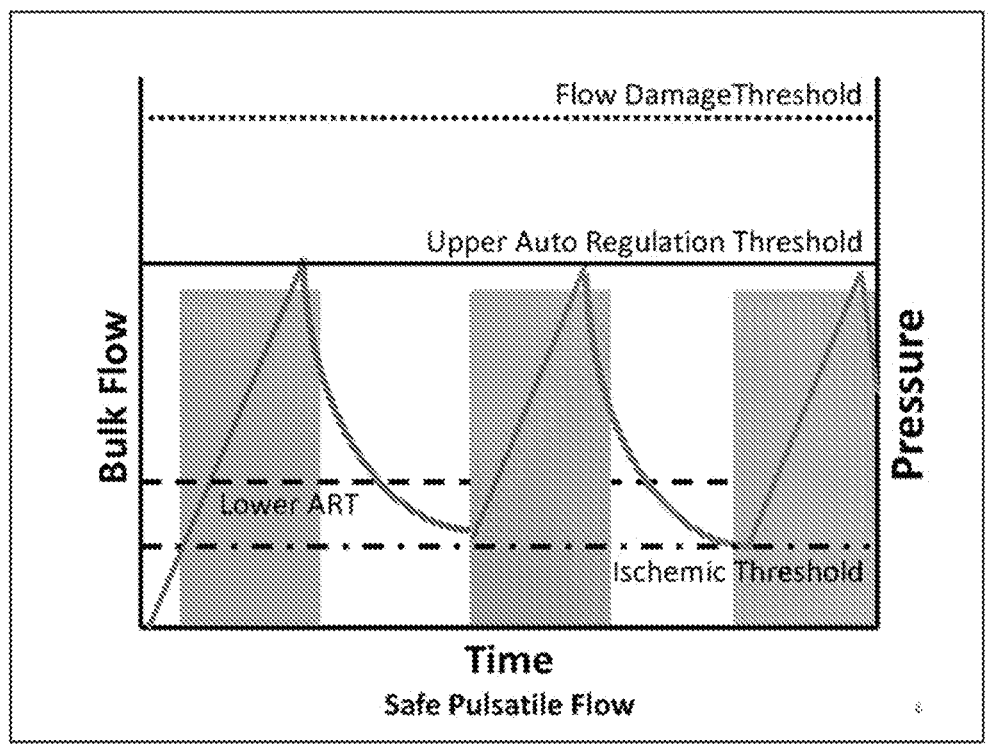
FIG. 10 is a chart depicting Bulk Flow: Pressure/Time; Safe Pulsitile Flow; with the physiological thresholds in place using the device disclosed.

FIG. 10 shows Bulk Flow: Pressure/Time; Safe Pulsitile Flow, with the physiological thresholds in place using the device disclosed.

Figure 11:
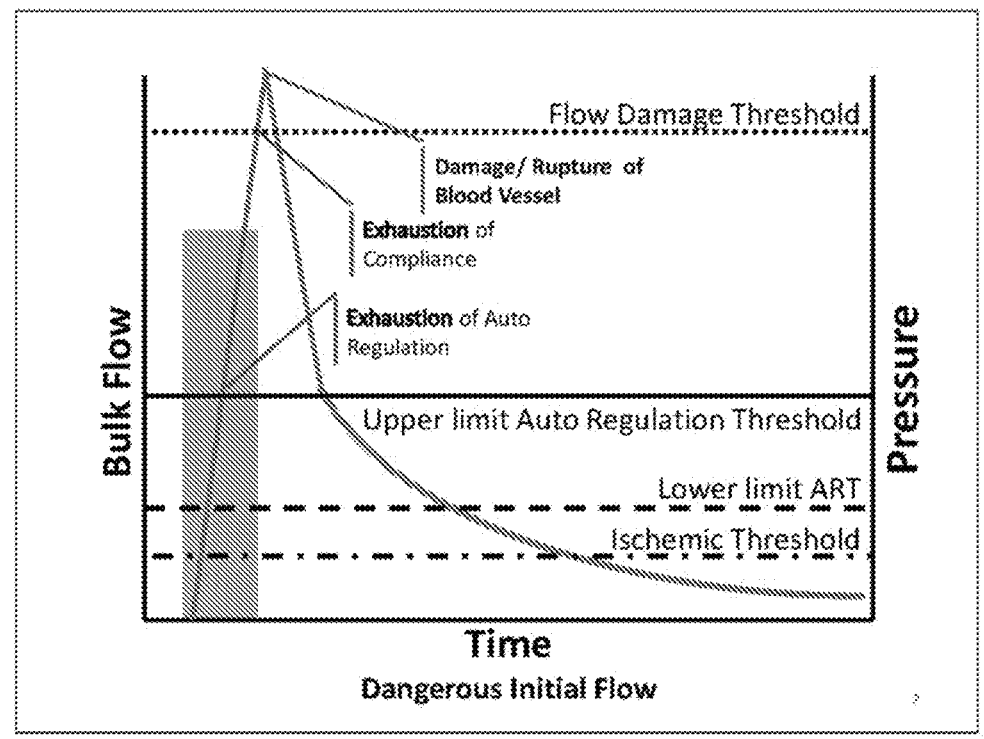
FIG. 11 is a chart depicting Bulk Flow: Pressure/Time; Dangerous Initial Flow. Showing that even a single short pulse of fluid can exceed the limits and cause rupture of a blood vessel. This is why injection distal to an occlusion is cautioned against in the clinical literature.

FIG. 11 shows Bulk Flow: Pressure/Time; Dangerous Initial Flow. Showing that even a single short pulse of fluid can exceed the limits and cause rupture of a blood vessel. This explains why injection distal to an occlusion is cautioned against in the clinical literature.

Figure 12:
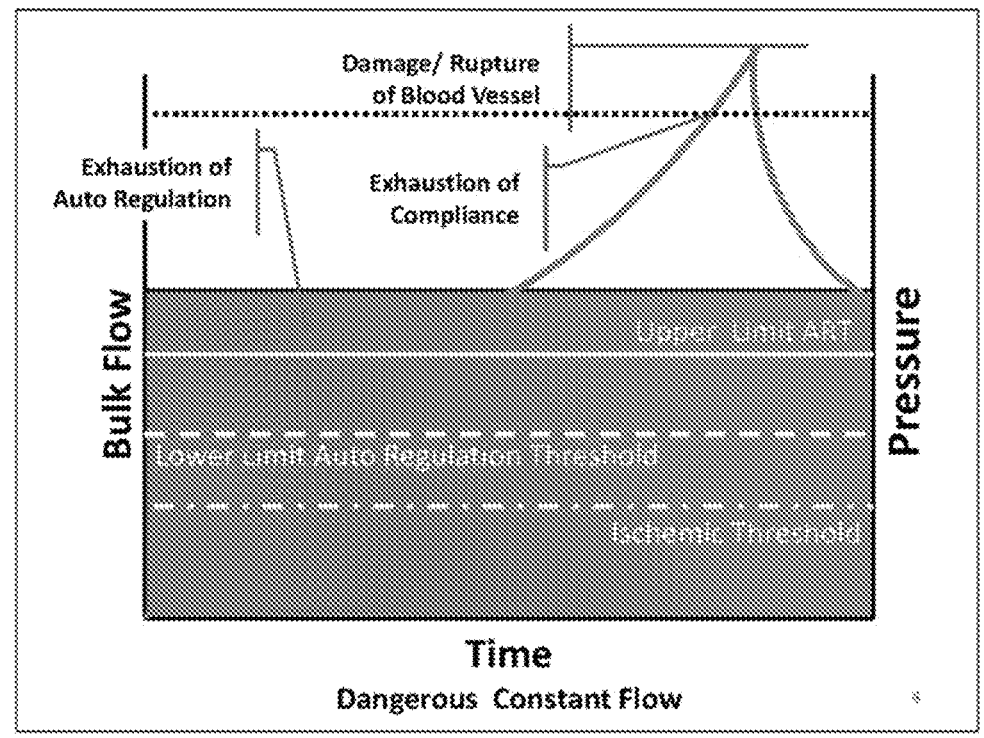
FIG. 12 is a chart depicting Bulk Flow: Pressure/Time; Dangerous Constant Flow. Even if the vessel does not immediately rupture, over time the flow can be exceeded overtime and transgress dangerous thresholds
Figure 13:
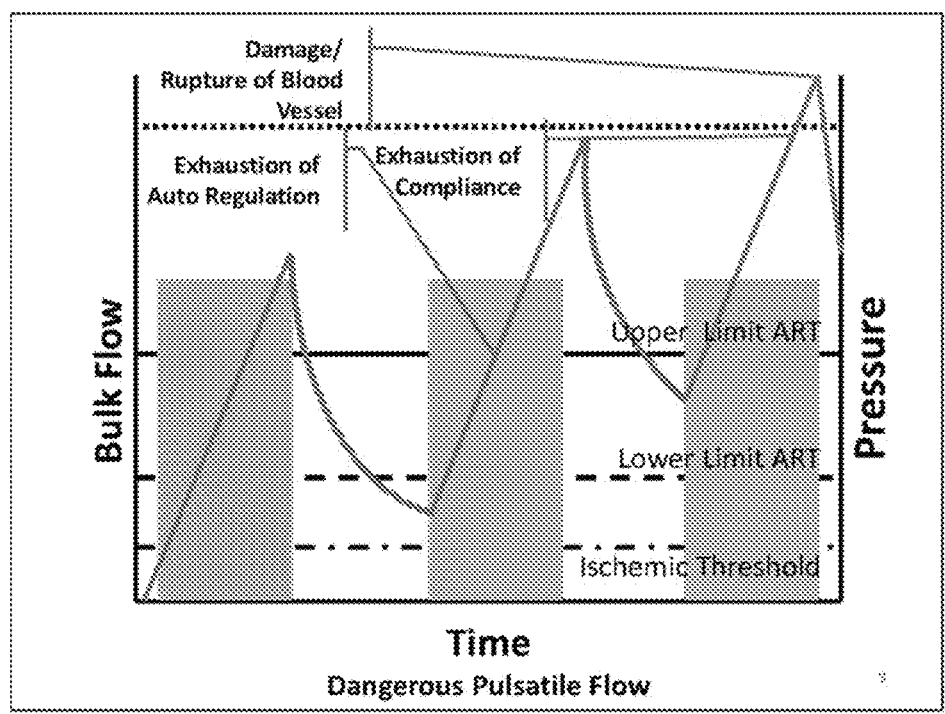
FIG. 13 is a chart depicting Bulk Flow: Pressure/Time; Dangerous Pulsitile Flow. Even if the vessel does not immediately rupture, over time the flow can be exceeded overtime and transgress dangerous thresholds
Figure 14:
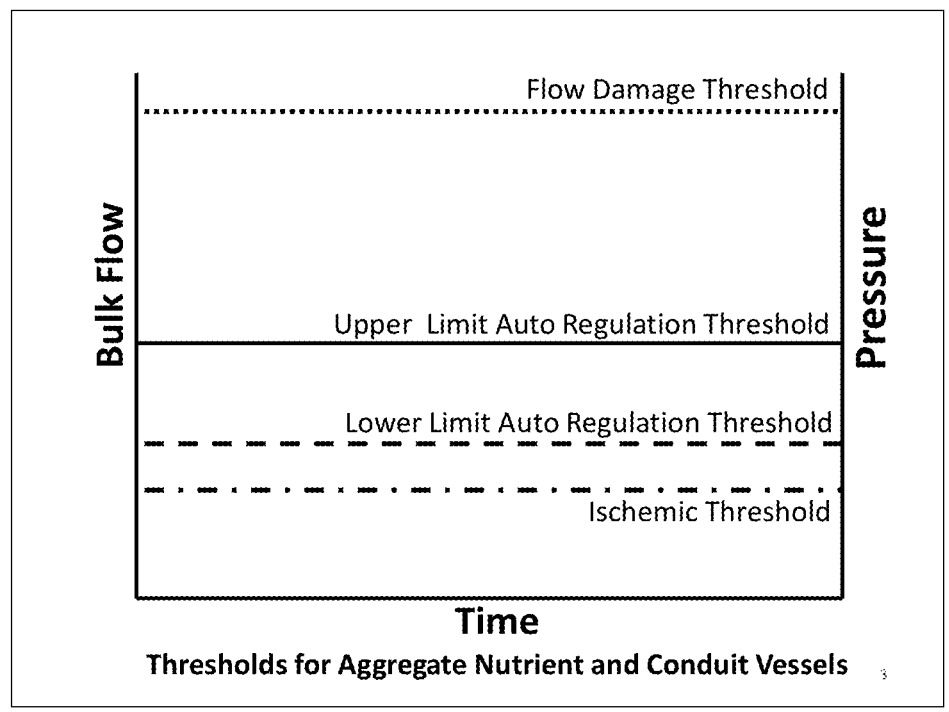
FIGS. 14-18 are charts depicting Flow Pressure/Time; showing the Thresholds.
Figure 15:
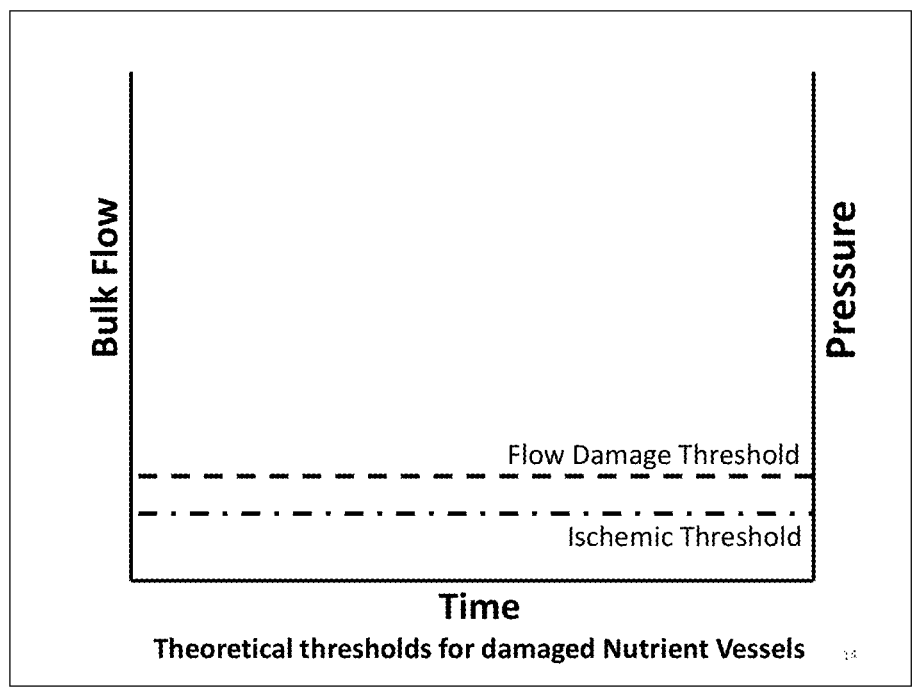
Figure 16:
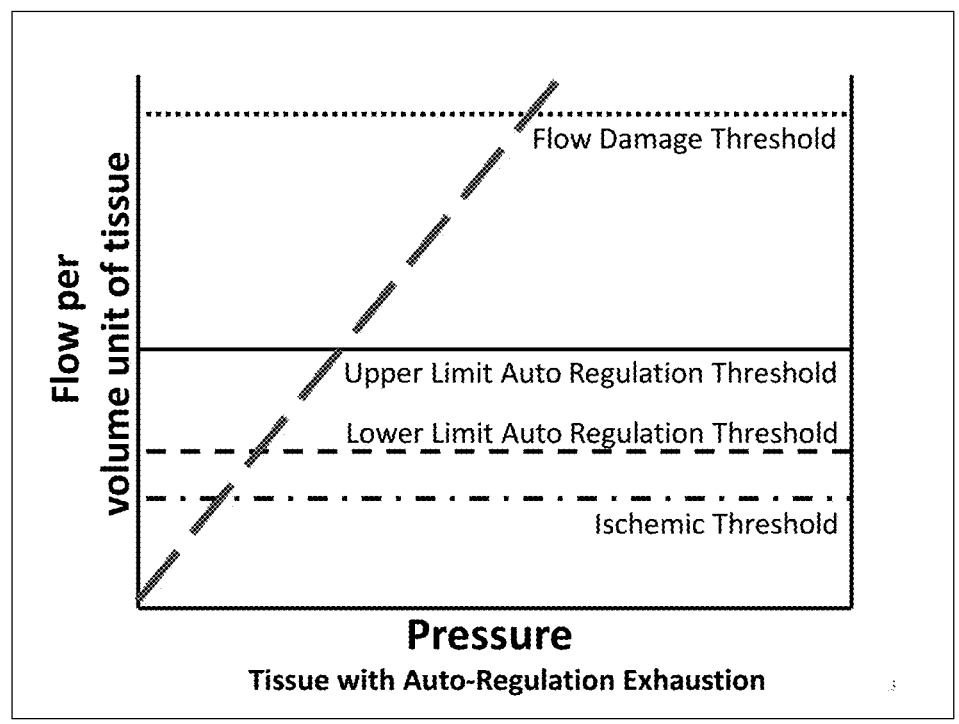

FIG. 12 shows Bulk Flow: Pressure/Time; Dangerous Constant Flow. Even if the vessel does not immediately rupture, over time the flow can be exceeded overtime and transgress dangerous thresholds FIG. 13 shows Bulk Flow: Pressure/Time; Dangerous Pulsitile Flow. Even if the vessel does not immediately rupture, over time the flow can be exceeded overtime and transgress dangerous thresholds FIGS. 14-15 show Flow Pressure/Time; showing the Thresholds. It should be noted that although the aggregate thresholds for conduit and nutrient vessels can be estimated, FIG. 14, it is quite likely that in damaged nutrient vessels the thresholds could be quite different.

Referring back to FIG. 1, the system according to at least one embodiment disclosed herein consists of a number of components, as well as a method to use this device. The system components generally includes:

1) A medical catheter, that can be placed or navigated into an artery, feeding the target tissue with perfusate at the flow, pressure, and other variables controlled by the system. The vessel is either already occluded, in which case the catheter is placed distal to the occlusion. In that situation where the vessel is not occluded, an enlargement of the distal tip adequate to occlude the target vessel is envisioned. In that situation where cold fluids are to be administered, insulation, and temperature measurement sensors would be incorporated. In one embodiment, the catheter would be a 5 French, 140 cc long, air-insulated, single high-pressure tolerant lumen catheter, with a soft tapered tip, mono-rail guided catheter placed through a guiding catheter into the cerebral circulation from a femoral approach. In another embodiment, the catheter would be a 5 French, 100 cc long, air-insulated, double lumen, distal balloon catheter, with a soft tapered tip, mono-rail guided catheter placed through a guiding catheter into the coronary circulation from a femoral approach. In another embodiment, the catheter would be a 7 French, 115 cc long, air-insulated, double lumen, distal balloon catheter, with a soft tapered tip, mono-rail guided catheter placed through a guiding catheter into the internal carotid circulation from a femoral approach and used for test occlusions, and during clot extraction.

2) Sensors include a near real-time pressure and flow measurement devices preferably at the distal end of the catheter. These can be either at the distal tip of the catheter, or more proximally, for example, in the catheter handle. If placed more proximally, correction for the resistance and compliance of the catheter must be integrated into the calculations performed by the system. Additional sensors could include, temperature sensors, $[O_2]$, etc. in the catheter and/or in the fluid reservoir, as well as bubble detectors. In one embodiment the temperature sensors will be located at the distal tip in the fluid pathway, and a second in the fluid reservoir, with pressure sensors being in the pump syringe to which the catheter interfaces, with correction for the resistance of the catheter and connecting tubing, and a servo-mechanism monitoring the amount of fluid injected. In another embodiment, the pressure, fluid rate and temperature sensors will be embedded distally in the catheter. Cost, size, and sensor technology will determine preferred embodiment.

3) The Pump is preferably a high precision, digitally controlled volume or pressure dependent pump. It is envisioned that when cold saline is infused, it will be a high-pressure pump to overcome the high resistance of the small diameter fluid conduit needed to decrease heat loss by transit time or enlarge the need for additional insulation. In this case, highly accurate corrections for the resistance of the catheter, and or distal pressure sensors would be needed. The pump requirements will depend on the particular clinical application. It is likely that one pump would not cover the entire range needed at a reasonable cost. However, description of such a pump would be a precisely controlled deliver to a 1 mmHg pressure, with a range of 0-60 mmHg delivered distally are required with flow rates from 0-150 cc per min and precisely controlled +/−5% cc/min flow rates. Additionally, safety valves or diverters are envisioned to be in place as back-up for pump malfunction.

4) Input and Output device is required to allow the operator to input and to have access to information regarding the procedure. A computer GUI may be used showing pertinent variables determined or otherwise computed by the system, as discussed herein, including temperature, pressure, flow, $[O_2]$, etc., distally or at the pump and/or reservoir, or any point in between. Additionally, audio and visual alarms may be incorporated separately.

5) Fluid Reservoir and Fluid Conditioner with Sensors; A fluid reservoir sufficient for storing and/or maintaining/conditioning the characteristics/parameters of the infusate, such as temperature, pressure, $[O_2]$, etc.

6) Computer Controller: A controller adequate to process the data captured and input by the user and/or looked up, to calculate the variables discussed herein for controlling the pump, and to control the pump based on such input and calculations/determinations.

7) Algorithms: The system is preferably programmed with processes that allow the calculation and control of perfusion distal to an occlusion. Specifically, by determining:

The infusate's parameters:
1. viscosity,
2. $[O_2]$, $[CO_2]$,
3. Temperature, and
4. The catheters Compliance, Resistance, and
5. The infused Volume vs. Pressure curve.

One or more of the following key parameters may be calculated based on the infusate parameters using the algorithms:
1) The amount of tissue being perfused.
2) The shape of the auto-regulation curve.
3) The amount of tissue that has intact vs. dysfunctional auto-regulation.
4) The tissue vascular compliance.
5) Estimates of critical thresholds.

The system may then then:
1. Control perfusion parameters to the tissue,
2. Within safe critical thresholds; and
3. Monitor for any critical changes and adjust accordingly.

Normal Blood Flow: Blood flow to tissue is dependent on the local vascular resistance. When the tissue needs more blood, the tissue blood vessels dilate, causing a drop in the local vascular resistance, and more blood flows to the tissue. Plugged arteries lead to strokes and heart attacks. A plugged vessel causes a large drop in the tissue blood pressure distal to the plug. When this happens the local blood vessels of the distal tissue profoundly dilate, causing a huge drop in the tissue vascular resistance, but it is not enough to maintain viable tissue blood flow. Gradations of this are present. The vascular bed is a network, and the blood flow of these blood vessels-distal to an occlusion, from other blood vessels not occluded, "collateral flow" is critical. The time and amount of tissue that the blood vessel serves is also important. The more the tissue blood flow is limited, and the longer time that the blood flow is limited the more likely that the tissue will die.

Figure 17:
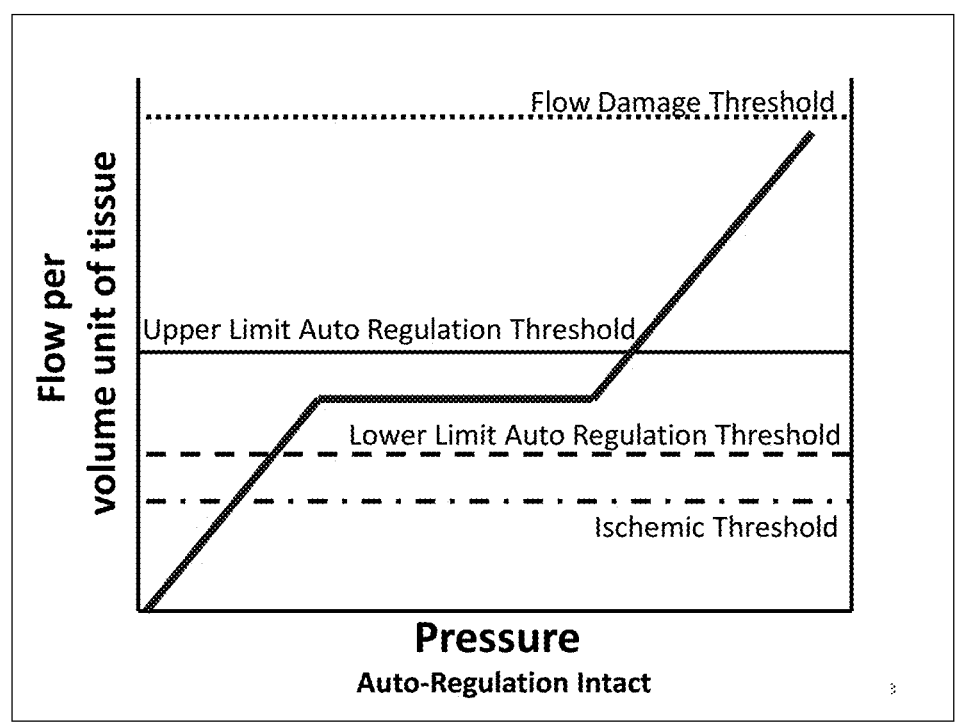
Figure 18:
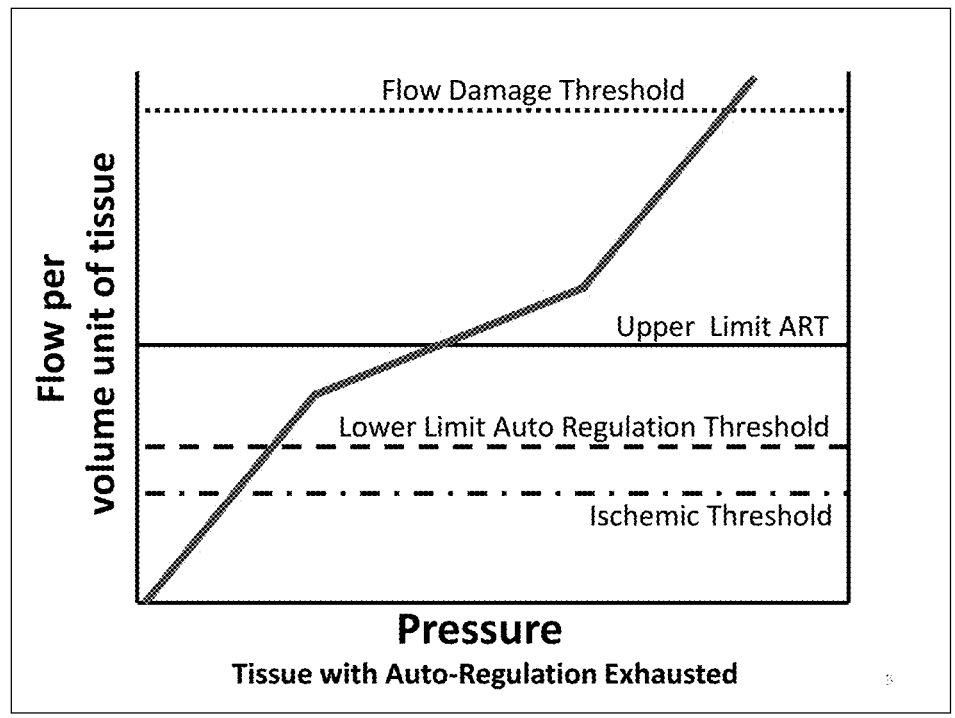

Auto-Regulation: Tissues, including the brain, heart, and kidneys auto-regulate the flow. This phenomenon is called Auto-regulation, keeps the blood flow constant over a large range of blood pressures. This is done by a change in the vascular resistance in response to the blood flow. The curve is characterized by an initial sloop, a plateau and a final slope. The first slope, ends at the Lower Limit of Auto-Regulation, LLA. The second slope, begins at the Upper Limit of Auto-Regulation, ULA. The slopes, $slope_{lower}$ and $slope_{upper}$, type of auto regulation curve are 1.7 and 2.0% change in CBF per mmHg/volume of tissue. Respectively. $Slope_{lower}$ is similar to the mean experimental data; $slope_{upper}$ is smaller. The curve can be appreciated from FIG. 3 showing the shape of auto-regulatory curve is altered by a number of metabolic components, including $[O_2]$, $[CO_2]$. It can also be altered by changes in the vascular bed brought on by hypertension, trauma, and stroke. Although not shown there, are also significant changes related to temperature, and viscosity of the blood. These effects are well characterized from extensive experimental data. In a tissue bed with exhausted autoregulation, the flow will be dependent on perfusion pressure, FIG. 16. It is known that at higher pressures, the risk of damaging the vessels and causing hemorrhage increases (Flow Damage Threshold), FIG. 14-18. Depending on the integrity of the vascular bed (type, intensity, and duration of injury) the Damage Threshold can vary, e.g. healthy (high threshold), ischemic injury (low threshold), traumatic injury (low threshold). Thus, there is an increased risk to reach Flow Damage Threshold in a compromised tissue bed with exhausted autoregulation because of reduction or complete absence of the wide range of pressure tolerance as seen in tissue beds with intact autoregulation (FIG. 17, 18).

Modeling Auto regulator curves: There are a number of mathematical models of the auto-regulator curves available, all of which could be used as a basis for the expected blood flow/min/tissue volume. Two models based on the physics of flow, are the fixed, or variable maximal vaso-reactivity. The variable maximal flow flow-pressure relationship above the upper-limit of Auto-regulation, ULA has the same slope as, and is thus parallel to, the relationship below the lower-limit auto-regulation, LLA. This is based on the fact that the CBF auto regulation curve most frequently described in the experimental literature shows such a parallel pattern A third-order polynomial by filling to the reported data for CBF-pressure curve can be calculated and used e.g., $$CBF=4.79\times10{-}5P3{-}1.74\times10{-}2P2{+}2.51P{-}38.8{-}$$
$$1.74\times10{-}2P2{+}2.51P{-}38.8.$$

This is limited as being non-explanatory, non-intuitive, and at the lower flow levels inaccurate.

When perfusing distal to an occlusion, the volume of tissue is not known. This volume of tissue must be calculated if the physiological measure flow/min/volume of tissue is to be determined. Additionally, unless the perfusate is blood, or a substance with a similar viscosity, the flow rate will be proportional altered. Equally problematic are the effects of temperature, $[O_2]$, $[CO_2]$, and the functioning of auto-regulation.

The problem, therefore, is calculating the flow/min/volume of tissue given the measured infused volume/pressure curve and the infusate's viscosity, $[O_2]$, $[CO_2]$, temperature, and devices compliance, resistance, identifying the new thresholds given the perfusion situation, and finally maintaining perfusion within these thresholds.

The present application discloses a system in this regard that does one or more of the following. 1) The normal, known and expected auto-regulatory curves for blood under normal conditions are inputted or looked up. 2) The slopes, plateaus and critical thresholds when blood is the infusate are inputted or looked up. 3) The factors that affect the infusion material flow, such as viscosity, and catheter characteristics are inputted or measured. 4) The factors that affect the tissue response to the perfusion materials flow such as $[O_2]$, $[CO_2]$, and tissue auto-regulatory status, are determined. 5) Given #3 and #4, the new expected pressure-volume/tissue perfused unit curve is calculated. 6) These values (#3, 4, and 5) are loaded into the computer to control the pump, with expected slopes, plateaus, and thresholds, per unit flow/pressure. 6) The device is placed, and infusion began and infusate volume pressure information is used to calculate the flow/min/volume of tissue.

In at least one embodiment, the method used to map the normal physiological blood-brain, auto-regulator curves to the infusate's volume/pressure curves could be differential calculus, linear algebra, or serial first order corrections. The preferred embodiment is serial first corrections as it is explanatory, intuitive, and simplest to execute and is taught in this.

A graphic presentation of these ideas can be seen in the figures that follow. FIGS. 5A1-5A3 shows how the amount of tissue perfused with oxygenated blood would alter the volume/pressure curve. FIGS. 5B1-B3 show how a low viscosity fluid such as saline that is adequately oxygenated would alter the volume pressure curves with different amounts of perfused tissue. FIGS. 5C1-5C3 similarly showed the effect of un-oxygenated saline, and tissue without regulation. FIGS. 5D1-5D3 shows the effect of temperature on metabolism, and thus the auto-regulatory curves. FIGS. 5E1-5E3 show how apparent thresholds for ischemia and hyperbaric-hyperemic thresholds can be determined. FIG. 6 shows the pressure time cure when a safe, effective constant volume of fluid is infused. FIG. 7 shows the thresholds that were respected. FIG. 8 shows the various thresholds that the system may prevent crossing. FIGS. 9 and 10 shows the device and method working within the thresholds in a constant and pulsitile mode. FIGS. 11, 12, 13 show possible failure modes transgressing thresholds. FIGS. 14-15 show that thresholds for aggregate vessels and nutrient vessels, may not be the same, and 16-18 instances with auto-regulation intact and exhausted.

Derivation of the Algorithms
Calculations for:
Determining cc of brain perfused, CBF,
when perfusing with Saline, at a temp of 37.8 C, invariant with $[O_2]$
For data from the initial portion of the Q/P curve,
Given Q/P curve,
Given:
a) Qbulk=P*Lπ(r)4/8η perfusate as measured by the disclosed device b) $Qcbf = P*L\dfrac{\pi(r)^4}{8\eta} \cdot /100 ccBrain$ as known from experimental literature.

c) L, π(r)4/8, is the same in both equations.
i) L, r, are the same at both ends of the auto P/V curve— where the blood vessels radius and length are maximally dilated.

ii) The shape of Qcbf/P curve is known under normal conditions [for blood with a η=3.6, [$O_2$]>4 cc/100 cc brain, temp=37.8, with intact auto-regulation etc.]
(1) For tissue with Auto-regulation; the slope of the initial (P=1-75 mmHg), and final P>175 mmHg) consistent with maximal dilation.
(2) For tissue with Auto-regulation; the slope of the middle portion of the curve, (175>P>75 mmHg) is zero
(3) For tissue without Auto regulation, or without $O_2$, the slope is similar to an over the entire P range with maximal dilation.
d) The initial and final Qcbf/P slope of approximately=55 cc/min/75 mmHg/100 cc of brain.
e) The compound slope for the blood flow/min per one unit of pressure and volume of brain:=0.0074 cc/min/1 mmHg/1 cc brain Note this represents the maximal slope of the system.
f) η perfusate is known, and for saline is 0.9 cp, or ¼ that of blood. Correcting for flow saline with the ¼ the viscosity will increase either the flow or the amount of brain perfused by 4× at the same pressure But since the vessels are maximally dilated, the amount of brain perfused must increase at the same pressure, or the pressure must decrease at the same perfusion. Since 4*0.0074 cc/min/1 mmHg/1 cc brain 0.0296 cc/min/1 mmHg/1 cc brain
g) Then 4*0.0074 cc/min/1 mmHg/1 cc brain must
  1. (0.0074 cc/min/0.25 mmHg/1 cc brain)=
  2. 0.0074 cc/min/1 mmHg/4 cc brain
h) Using this it is possible to determine the volume of brain being perfused with the infusate with the viscosity that is ¼ that of blood at a given pressure gradient: (Qbulk/P)/(0.0074 cc/min/0.25 mmHg/1 cc brain)=cc of brain perfused
i) Example; if a vessel infused with 37.8° C. Saline and gives the following:

$$Qbulk/P = (20\,cc/min)/(10\,mmHg)$$

$$\text{Then volume of brain} = (20\,cc/min)/(10\,mmHg)/\big((0.0074\,cc/min)/(0.25\,mmHg/1\,cc\,brain)\big)$$
$$= 67.6\,cc\,brain$$

$$\text{Then the } CBF \text{ in cc/min/100 cc brain is} = (20\,cc/min)/(67.6\,cc/100\,cc\,brain)$$
$$= 29.6\,cc/min/100\,cc\,brain/$$

Given the above it is possible to explore the expected ischemic thresholds, expected hyperbaric threshold, expected hyperemic threshold, inflection point of the auto-regulator curve, and the effect of temperature on metabolic rate and thus CBF, Exemplary calculations for determining expected ischemic thresholds:

Given the brains needs 4 cc $O_2$/100 cc brain/min of available $O_2$@37.8° C. Note, this assumes that all dissolved $O_2$ is available, which is a simplification for saline, but not for blood which is a rough approximation. $O_2$ content can be calculated by the solubility time partial pressure. Thus, the ischemic threshold is 0.04 cc $O_2$/1 cc brain/min then, 67.6 cc brain needs (67.6 cc brain)×(0.04 cc $O_2$/1 cc brain/min) or the ischemic threshold of this tissue at this flow requires the infused saline has [$O_2$]=2.7 cc. Given that there is approximated 0.034 cc [$O_2$]/100 cc saline, thus 0.0034 cc [$O_2$]/1 cc saline×67.6 cc brain=0.23 cc in the infused saline. Thus, the ischemic threshold of 2.7 cc is not met by 0.23 cc $O_2$/min/1 cc brain being infused. If the ischemic threshold is not met, the slope of the Q/V curve remains unchanged.

The ischemic threshold can be met by: 1)—increasing the flow by increasing the pressure, 2)—lowering the threshold by lowering the metabolic rate, $CMRO_2$, or 3) increasing the dissolved $O_2$. Each of these independently could, theoretically be increased by a factor of 12, (2.7/0.23). Increasing the pressure by a factor of 12 or to 120 mmHg (12×10 mmHg) will meet the ischemic threshold. But this will damage tissue as the hyperemic threshold is exceeded. The hyperemic threshold is difficult if not impossible to separate from the hyperbaric threshold, and at a tissue level, likely to be nearly synonymous. For our purposes, we will consider the flow and or the pressure as the acting as independent damaging thresholds. The exact flow nature of the flow rate above which tissue capillaries, etc. are damaged is unclear, however, estimates place it at approximately 100-120 cc/min/100 cc brain, or 1-1.2 cc/min/1 cc of brain.

Given that in this example, the flow of to the brain is 29.6 cc/min/100 cc brain, and the expected hyperemic threshold will be met at 100-120 cc/min/100 cc brain, the pressure can only be increase by a factor of 3-4 before hyperemic damage can be expected, or a pressure of 30-40 mmHg. Note, hyperbaric thresholds appear to be in the range of 200-220 mmHg, although higher in the chronic hypertensive, and lower in tissue that is not performing auto-regulation. Thus: The new ischemic threshold is ½ of 0.04 cc $O_2$/1 cc brain/min or 0.02 cc $O_2$/min/1 cc brain; 67.6 cc brain needs (67.6 cc brain)×(0.02 cc $O_2$/1 cc brain/min); or the ischemic threshold of this amount of tissue at this flow requires the infused saline has [$O_2$]=1.35 cc $O_2$/min. Given that there is approximated 0.34 cc [$O_2$]/100 cc saline thus 0.0034 cc [$O_2$]/1 cc saline/min×67.6 cc brain=0.23 cc $O_2$/min in the infused saline.

The ischemic threshold can be met with the use of hyperbaric, increasing the partial pressure of $O_2$. The partial pressure of $O_2$ at room air under normal physiological conditions approximately 100 mmHg. Without the spectacularly efficient $O_2$ caring capacity of Hemoglobin, the [$O_2$] could only be derived from the dissolved oxygen in the fluid, and in this example, the saline. At 3 ATP, the partial pressure of $O_2$ increases by a factor of approximately 20. In this example, the ischemic threshold could be reached by increasing the partial pressure of the $O_2$ in the saline to approximately 2 ATP. Such super-saturated fluid would bubble spontaneously.

The ischemic threshold can also be met at lower flow rates by the use of hypothermia. Hypothermia, in cooling the saline has three effects; 1) it decreases the CMR by approximately 10%/1° C., 2) It increases the solubility of $O_2$ by approximately 1.5%/1° C., and 3) increases the viscosity by 1.5%/1° C. (The effects of cooling on viscosity and solubility can, for this example are ignored since they are small, similar in size, and could have opposite effects on $O_2$ delivery).

Example: Given using the example above, assume we cool the temperature of the fluid to 25° C., and assume the brain quickly reaches this lower temperature. This will decrease the $CMRO_2$ by approximately 75%, which will decrease the [$O_2$] needed by a, and thereby lowing the ischemic threshold by 50%.

Tissue Conditioning: Tissue at risk for ischemic injury and secondary injury related to ischemia may be conditioned by controlled and repeated reduction of tissue temperature distal to the arterial occlusion under monitoring of above parameters. Hereby, arterial occlusion may be a pathological condition, e.g. ischemic stroke/infarct, or created artificially, e.g. balloon occlusion. Between the phases of temperature reduction are pauses to allow the tissue temperature to return to higher temperatures. By doing so, tissue at risk may be prepared to better withstand the consequences arising from ischemia and reperfusion.

While the foregoing invention has been described in some detail for purposes of clarity and understanding, it will be appreciated by one skilled in the art, from a reading of the disclosure, that various changes in form and detail can be made without departing from the true scope of the invention.

What is claimed is:

1. A system for perfusing blood vessels distal to an occlusion comprising:
    a pump coupled to an insertion device and a fluid reservoir, the pump operable therewith to supply an infusate stored in the fluid reservoir to the insertion device distal to an occlusion in a blood vessel;
    a controller operatively coupled to the pump; and
    a plurality of sensors operatively coupled to the controller, the controller having memory associated therewith that stores an instruction set that when executed causes the controller to:
    determine a pressure in the blood vessel based on input from at least one of the plurality of sensors,
    calculate tissue parameters and physiological thresholds of tissue distal to the occlusion, and
    control the pump to maintain perfusion volume and perfusion pressure distal to the occlusion within the physiological thresholds based on real-time feedback from the plurality of sensors, wherein the physiological thresholds comprise an ischemic threshold and an autoregulation threshold for the tissue being perfused.

2. The system of claim 1, wherein the insertion device is a catheter.

3. The system of claim 2, wherein the plurality of sensors comprise at least one temperature sensor for measuring temperature of the infusate at a distal end of the catheter.

4. The system of claim 2, wherein the plurality of sensors comprise at least one sensor for measuring infusate flow at a distal end of the catheter.

5. The system of claim 2, wherein the plurality of sensors are located proximal relative to a distal end of the catheter and wherein the controller determines corrections for at least one of resistance and compliance of the catheter and further controls the pump based on the resistance and compliance determinations.

6. The system of claim 1, comprising an input device configured to receive user input with regard to operating parameters of the system.

7. The system of claim 1, comprising an output device, the controller further operable to display at the output device a graphic user interface comprising the calculated tissue parameters.

8. The system of claim 7, wherein the insertion device is a catheter, the controller further operable to display at the output device at least one of: infusate temperature, infusate pressure, infusate flow, and infusate [O2], measured at a distal end of the catheter, the pump, or at the fluid reservoir.

9. The system of claim 1, the controller further operable to determine infusate parameters, calculate the tissue parameters based on the infusate parameters, and control perfusion based on the tissue parameters.

10. The system of claim 9, wherein the insertion device is a catheter, and wherein the infusate parameters comprise at least one of: infusate viscosity, infusate [O2], infusate [CO2], infusate temperature, catheter compliance, catheter resistance, and an infused Volume vs. Pressure curve.

11. The system of claim 10, wherein the tissue parameters comprise at least one of: an auto-regulation curve, tissue vascular compliance, and at least one threshold regarding infusate flow and pressure.

12. The system of claim 11, the controller controls infusate flow and pressure based on the tissue parameters within the calculated ischemic and autoregulation thresholds.

13. The system of claim 1, the controller further operable to determine an initial stump pressure distal to the occlusion, incrementally increase at least one of the perfusion volume and perfusion pressure from the initial stump pressure, and calculate volume of tissue being perfused.

14. The system of claim 13, the controller further operable to estimate an autoregulation inflection point of the tissue being perfused.

15. The system of claim 13, the controller further operable to calculate vascular compliance and to control the pump to operate within vascular compliance boundary conditions.

16. The system of claim 13, the controller further operable to estimate an autoregulation inflection point of the tissue being perfused and to control the pump to operate between the ischemic threshold and the autoregulation inflection point.

17. The system of claim 1, wherein the autoregulation threshold comprises lower and upper autoregulation thresholds, and the controller controls infusate flow and pressure based on the tissue parameters within the calculated ischemic and upper autoregulation thresholds.

18. The system of claim 1, wherein the autoregulation threshold comprises lower and upper autoregulation thresholds, and the controller controls infusate flow and pressure based on the tissue parameters within the calculated lower and upper autoregulation thresholds.

* * * * *